United States Patent
Yodh et al.

(10) Patent No.: US 8,082,015 B2
(45) Date of Patent: Dec. 20, 2011

(54) OPTICAL MEASUREMENT OF TISSUE BLOOD FLOW, HEMODYNAMICS AND OXYGENATION

(75) Inventors: Arjun G. Yodh, Merion, PA (US); Joel H. Greenberg, Wayne, PA (US); Guoqiang Yu, Flemington, NJ (US); John A Detre, Wynnewood, PA (US); Turgut Durduran, Upper Darby, PA (US); Mark G. Burnett, Philadelphia, PA (US); Emile R. Mohler, III, Radnor, PA (US); Harry Quon, Rose Valley, PA (US); Stephen M. Hahn, Glen Mills, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 918 days.

(21) Appl. No.: 11/106,390

(22) Filed: Apr. 13, 2005

(65) Prior Publication Data
US 2006/0063995 A1    Mar. 23, 2006

Related U.S. Application Data

(60) Provisional application No. 60/561,758, filed on Apr. 13, 2004.

(51) Int. Cl.
*A61B 5/00* (2006.01)
*G01N 21/25* (2006.01)
(52) U.S. Cl. ........ 600/310; 600/323; 600/328; 600/344; 600/407; 600/473; 600/474; 600/475; 600/476; 600/477; 356/406; 356/477
(58) Field of Classification Search .............. 600/310, 600/323, 328, 344, 407, 473–477; 356/406, 356/477
See application file for complete search history.

(56) References Cited

U.S. PATENT DOCUMENTS

| | | | | |
|---|---|---|---|---|
| 4,109,647 A | * | 8/1978 | Stern et al. | 600/479 |
| 4,170,987 A | * | 10/1979 | Anselmo et al. | 600/475 |
| 4,281,645 A | * | 8/1981 | Jobsis | 600/324 |

(Continued)

FOREIGN PATENT DOCUMENTS
EP    0 947 822 A1    10/1999

OTHER PUBLICATIONS

Boas, D.A.; Dale, A.M.; Franceschini, M.A.; Diffuse optical imaging of brain activation: approaches to optimizing image sensitivity, resolution, and accuracy; NeuroImage, 2004; vol. 23, pp. S275-S288.*

Boas, D.A.; Yodh, A.G.; Spatially varying dynamical properties of turbid media probed with diffusing temporal light correlation; Journal of the Optical Society of America; Jan. 1997; A/vol. 14, pp. 192-215.*

(Continued)

*Primary Examiner* — Unsu Jung
(74) *Attorney, Agent, or Firm* — Woodcock Washburn, LLP

(57) ABSTRACT

An embodiment of the invention includes a device, system and method for determining the characteristics of deep tissue. The novel method includes measuring blood flow rate and oxygenation characteristics of the tissue, and determining oxygen metabolism of the tissue as a function of the measure blood flow rate and measure oxygenation. The blood flow rate characteristics are measured as a function of light fluctuations caused by the tissue, while the oxygenation characteristics are measured as a function of transmission of light through the tissue with respect to the wavelength of light. The tissue may be layered tissue, for example, a portion of a brain. The tissue characteristics may be measured during times of varying levels of exercise intensity.

42 Claims, 10 Drawing Sheets

U.S. PATENT DOCUMENTS

| | | | | | |
|---|---|---|---|---|---|
| 4,321,930 | A | * | 3/1982 | Jobsis et al. | 600/344 |
| 4,515,165 | A | * | 5/1985 | Carroll | 600/475 |
| 4,824,242 | A | * | 4/1989 | Frick et al. | 356/41 |
| 4,972,331 | A | * | 11/1990 | Chance | 600/310 |
| 4,975,237 | A | * | 12/1990 | Watling | 356/338 |
| 5,122,974 | A | * | 6/1992 | Chance | 600/323 |
| 5,203,339 | A | * | 4/1993 | Knuttel et al. | 600/425 |
| 5,213,105 | A | * | 5/1993 | Gratton et al. | 600/473 |
| 5,309,907 | A | * | 5/1994 | Fang et al. | 600/342 |
| 5,424,843 | A | * | 6/1995 | Tromberg et al. | 356/442 |
| 5,598,841 | A | * | 2/1997 | Taniji et al. | 600/342 |
| 5,625,458 | A | * | 4/1997 | Alfano et al. | 356/446 |
| 5,673,701 | A | * | 10/1997 | Chance | 600/473 |
| 5,920,390 | A | * | 7/1999 | Farahi et al. | 356/477 |
| 6,058,324 | A | * | 5/2000 | Chance | 600/473 |
| 6,076,010 | A | | 6/2000 | Boas et al. | 600/477 |
| 6,411,907 | B1 | * | 6/2002 | Lu et al. | 702/28 |
| 6,542,772 | B1 | * | 4/2003 | Chance | 600/473 |
| 6,640,133 | B2 | * | 10/2003 | Yamashita et al. | 600/476 |
| 6,694,159 | B2 | * | 2/2004 | Hall et al. | 600/310 |
| 6,831,741 | B1 | * | 12/2004 | De Kruif et al. | 356/338 |
| 6,985,763 | B2 | * | 1/2006 | Boas et al. | 600/323 |
| 7,616,984 | B2 | * | 11/2009 | Barbour et al. | 600/473 |
| 2006/0155193 | A1 | * | 7/2006 | Leonardi et al. | 600/473 |
| 2010/0056936 | A1 | * | 3/2010 | Fujii et al. | 600/504 |

OTHER PUBLICATIONS

Culver, Joseph P. ; Durduran, Turgut ; Furuya, Daisuke ; Cheung, Cecil ; Greenberg, Joel H. ; Yodh, A. G.; Diffuse optical tomography of cerebral blood flow, oxygenation, and metabolism in rat during focal ischemia; Journal of Cerebral Blood Flow & Metabolism, 2003; vol. 23, pp. 911-924.*

Abels, C., et al., "In vivo kinetics and spectra of 5-aminolavulinic acid-induced fluorescence in an amelanotic melanoma of the hamster," *British J. of Cancer*, 1994, 70, 826-833.

Ahonen, J., et al., "Brain injury after adult cardiac surgery," *Acta Anaesthesiol Scan*, 2004, 48, 4-19.

American-Cancer-Society, "Cancer facts and figures 2002," http://www.cancer.org/downloads/STT/CancerFacts&Figures2002TM.pdf202, 2 pages.

Ances, B.M., et al., "Dynamic changes in cerebral blood flow, O-2 tension and calculated cerebral metabolic rate of O-2 during functional activation using oxygen phosphorescence quenching," *J. of Cerebral Blood Flow & Metabolism*, 2001, 21, 511-516.

Arnfield, M.R., et al., "Optical properties of experimental prostate tumors in vivo," *Photochem. & Photobiol.*, 1993, 57(2), 306-311.

Arnfield, M.R., et al., "Optical dosimetry for interstitial photodynamic therapy," *Medical Physics*, 1989, 16(4), 602-608.

Arnfield, M.R., et al., "Optical propagation in tissue with anistropic scattering," *IEEE Trans. on Biomed. Eng.*, 1988, 35(5), 372-381.

Arnfield, M.R., et al., "Analysis of tissue optical coefficients using an approximate equation valid for comparable absorption and scattering," *Phys. Med. Biol.*, 1992, 37(6), 1219-1230.

Arnfield, M.R., et al., "The impact of electron transport on the accuracy of computed dose," *Med. Physics*, 2000, 27(6), 1266-1274.

Arnfield, M.R., et al., "Photodynamic therapy dosimetry in postmortem and in vivo rat tumors and an optical phantom," *Photochem. & Photobiol.*, 1990, 51(6), 667-674.

Arridge, S.R., "Optical tomography in medical imaging," *Inverse Problems*, 1999, 15, R41-R93.

Astrand, P.-O., et al., *Textbook of Work Physiology*, 4th Ed., Michael, S.B., et al. (Eds.), 2003, 146-148.

Barbier, E.L., et al., "Perfusion imaging using dynamic arterial spin labeling (DASL)," *Mag. Res. in Med.*, 2001, 45, 1021-1029.

Barbour, R., et al., "Optical tomographic imaging of dynamic features of dense-scattering media," *J. Optical Soc. Am. A*, 2001, 18(12), 3018-3036.

Bays, R., et al., "Light dosimetry for photodynamic therapy in the esophagus," *Lasers in Surgery & Medicine*, 1997, 20, 290-303.

Bellinier, D.A., et al., "Design and construction of a light-delivery system for photodynamic therapy," *Medical Physics*, 1999, 26(8), 1552-1558.

Belliveau, J.W., et al., "Functional mapping of the human visual cortex by magnetic resonance imaging," *Science*, 1991, 254, 716-719.

Benaron, D.A., et al., "Noninvasive functional imaging of human brain using light," *J. of Cerebral Blood Flow & Metabolism*, 2000, 20, 469-477, http://www.nature.com, 20 pages.

Berne, B.J., et al., *Dynamic Light Scattering with Applications to Chemistry, Biology, and Physics*, Krieger, Malabar, FL, 1990, table of contents (v-vii) and Chapter 1, 3-9.

Bertolotti, B.., et al., "Light scattering by particles suspended in a turbulent fluid" *J. Phys. A (Gen. Phys.)*, 1969, 2(2), 126-128.

Bevilacqua, F., et al., "In vivo local determination of tissue optical properties: applications to human brain," *Applied Optics*, 1999, 38, 4939-4950.

Binggeli, C., et al., "Statins enhance postischemic hyperemia in the skin circulation of hypercholesterolemic patients: a monitoring test of endothelial dysfunction for clinical practice?," *J. Am. Coll. Cardiol.*, 2003, 42(1), 71-77.

Binzoni, T., et al., "Non-invasive laser Doppler perfusion measurements of large tissue volumes and human skeletal muscle blood RMS velocity," *Phys. Med. Biol.*, 2003, 48, 2527-2549.

Binzoni, T., et al., "Metabolic studies of human skeletal muscle by near infrared spectroscopy: possible applications in space research," *Int. J. Sports Med.*, 1997, 18(Suppl. 4), S312-S314.

Binzoni, T., et al., "Non-standard $O_2$ consumption-temperature curves during rest and isometric exercise in human skeletal muscle," *Comp. Biochem. Physiol. A mol. Integr. Physiol.*, 2002, 132, 27-32.

Binzoni, T., et al., "Energy metabolism and interstitial fluid displacement in human gastrocnemius during short ischemic cycles," *J. Appl. Physiol.*, 1998, 1244-1251.

Binzoni, T., et al., "A new combined deep-body-temperature/NIRs probe for noninvasive metabolic measurements on human skeletal muscle," *Adv. Exp. Med. Biol.*, 1999, 471, 623-629.

Boas, D.A., et al., "Diffuse photon probes of structural and dynamical properties of turbin media: theory and biomedical applications" *Disclosure No. I1475*, 1996, iii-xvi.

Boas, D.A., et al., "Can the cerebral metabolic rate of oxygen by estimated with near-infrared spectroscopy?," *Phys Med. Biol.*, 2003, 48, 2405-2418.

Boas, D.A., et al., "Scattering and imaging with diffusing temporal field correlations," *Phys. Rev. Letts.*, 1995, 75(9), 1855-1858.

Boas, D.A., et al., "Spatially varying dynamical properties of turbid media probed with diffusing temporal light correlation," *J. Opt. Soc. Am. A*, 1997, 14(1), 192-215.

Boas, D.A., et al., "The accuracy of near infrared spectroscopy and imaging during focal changes in cerebral hemodynamics," *NeuroImage*, 2001, 13, 76-90.

Boas, D.A., et al., "Imaging the body with diffuse optical tomography," *IEEE Signal Processing Magazine*, 2001, 18, 57-75.

Bonner, R., et al., "Model for laser Doppler measurements of blood flow in tissue," *Applied Optics*, 1981, 20(12), 2097-2107.

Bonner, R.F., et al., "Principles of laser-Doppler blood flowmetry," *Kluwer Acad. Publ.*, Boston, 1990, vol. 107, 17-45.

Bourke, P.J., "A study of the spatial structure of turbulent flow by intensity-fluctuation spectroscopy," *J. Phys. A*, 1970, 3, 216-228.

Braichotte, D., et al., "Clinical pharmacokinetic studies of tetra(meta-hydroxphenyl)chlorine in squamous cell carcinoma by fluorescence spectroscopy at 2 wavelengths," *International J. of Cancer*, 1995, 63, 198-204.

Braichotte, D.R., et al., "Clinical pharmacokinetic studies of photofrin by fluorescence spectroscopy in the oral cavity, the esophagus, and the bronchi," *Cancer*, 1995, 75(11), 2768-2778.

Braichotte, D.R., et al., "Optimizing light dosimetry in photodynamic therapy of early stage carcinomas of the esophagus using fluorescence spectroscopy," *Lasers in Surgery & Medicine*, 1996, 19, 340-346.

Bramlett, H.M., et al., "Pathophysiology of cerebral ischemia and brain trauma: similarities and differences," *J. Cereb. Blood Flow Metab.*, 2004, 24, 133-150.

Brasseur, N., et al., "Photodynamic activities and skin photosensitivity of the bis(dimethylthexylsiloxy)silicon 2,3-naphthalocyanine in mice," *Photochemistry * Photobiology*, 1995, 62(6), 1058-1065.

Briers, J.D., "Laser Doppler, speckle and related techniques for blood perfusion mapping and imaging," *Physiol. Meas.*, 2001, 22, R35-R66.

Brown, W., *Dynamic Light Scattering: the Method and Some Applications*, Clarendon, NY, 1993, Table of Contents, xv-xiii.

Burchert, W., et al., Oxygen-15-water PET assessment of muscular blood flow in peripheral vascular disease, *J. Nucl. Med.*, 1997, 38(1), 93-98.

Buxton, R.B., et al., "A model for coupling between cerebral blood flow and oxygen metabolism during neuronal stimulation," *J. of Cerebral Blood Flow & Metabolism*, 1997, 17, 64-72, http://www.nature.com, 17 pages.

Catalona, W.J., "Screening for early detection of prostate cancer," *Lancet*, 1996, 347, p. 1629.

Catalona, W.J., "Management of cancer of the prostate," *New Engl. J. of Med.*, 1994, 331, 996-1004, http://proxy.library.upenn.edu:8170, 19 pages.

Catalona, W.J., "Conservative management of prostate cancer," *New Engl. J. of Med.*, 1994, 330(25), 1830-1832, http://proxy.library.upenn.edu:8170, 5 pages.

Cerretelli, P., et al., "The contribution of NMR, NIRS and their combination to the functional assessment of human muscle," *Int. J. Sports Med.*, 1997, 18, S270-S279.

Chance, B., et al., "Recovery from exercise-induced desaturation in the quadriceps muscles of elite competitive rowers," *Am. J. Physiol.*, 1992, 262, C766-C775.

Chance, B., "Near-infrared images using continuous, phase-modulated, and pulsed light with quantitation of blood and blood oxygenation," *Adv. Opt. Biop. and Opt. Mammography, Ann. of NY Acad. of Sci.*, 1998, 838, 29-45.

Chance, B., et al., "$^{31}$P NMR studies of control of mitochondrial function in phosphofructokinase-deficient human skeletal muscle," *Proc. Natl. Acad. Sci. USA*, 1982, 79, 7714-7718, http://www.jstor.org, 9 pages.

Chance, B., et al., "Mitochondrial regulation of phosphocreatline/inorganic phosphate ratios in exercising human muscle: a gated $^\wedge$ {31P}$P NMR study," *Proc. Natl. Acad. Sci. USA*, 1981, 78, 6714-6718.

Chance, B., et al., "Time-resolved spectroscopy of hemoglobin and myoglobin in resting and ischemic muscle," *Anal. Biochem.*, 1988, 174, 698-707.

Chance, B., et al., "A novel method for fast imaging of brain function, non-invasively, with light," *Optics Express*, 1998, 2, 411-423.

Chen, Q., et al., "Changes in in vivo optical properties and light distributions in normal canine prostate during photodynamic therapy," *Radiation Research*, 1997, 147, 86-91.

Chen, Q., et al., "Laser dosimetry studies in the prostate," *J. Clin. Laser Med. Surg.*, 1998, 16(1), 9-12.

Chen, Q., et al., "Preclinical studies in normal canine prostate of a novel palladium-bacteriopheophorbide (WST09) photosensitizer for photodynamic therapy of prostate cancers," *Photochem. & Photobio.*, 2002, 76(4), 438-445.

Chen, Q., et al., "The effect of light fluence rate in photodynamic therapy of normal rat brain," *Radiation Res.*, 1992, 132, 120-123.

Chen, Q., et al., "Damage threshold of normal rat brain in photodynamic therapy," *Photochem. & Photobiol.*, 1996, 64(1), 163-167.

Chen, Q., et al., "Effects of light beam size on fluence distribution and depth of necrosis in superficially applied photodynamic therapy of normal rat brain," *Photochem. & Photobiol.*, 1992, 56(3), 379-384.

Cheung, R., et al., "Correlation of in vivo photosensitizer fluorescence and photodynamic-therapy-induced depth of necrosis in a murine tumor model," *J. of Biomed. Optics*, 2003, 8(2), 248-252.

Cheung, C., et al., "In vivo cerebrovascular measurement combining diffuse near-infrared absorption and correlation spectroscopies," *Physics in Med. and Biol.*, 2001, 46, 2053-2065.

Cicoira, M., et al., "Skeletal muscle mass independently predicts peak oxygen consumption and ventilatory response during exercise in noncachectic patients with chronic heart failure," *J. Am. Coll. Cardiol.*, 2001, 37(8), 2080-2085.

Clark, N.A., et al., "A study of Brownian motion using light scattering," *Am. J. of Phys.*, 1970, 38(6), 575-585.

Colak, S.B., et al., "Clinical optical tomography and NIR spectroscopy for breast cancer detection," *IEEE J. of Selected Topics in Quantum Electronics*, 1999, 5(4), 1143-1158.

Coles, J.P., et al., "Incidence and mechanisms of cerebral ischemia in early clinical head injury," *J. Cereb. Blood Flow Metab.*, 2004, 24, 202-211.

Colebatch, J.G., et al., "Regional cerebral blood flow during voluntary arm and hand movements in human subjects,"*J. Neurophysiol.*, 1991, 65(6), 1392-1401.

Cope, M., et al., "System for long-term measurement of cerebral blood flow and tissue oxygenation on newborn infants by infra-red transillumination," *Med. & Biol. Eng. Comput.*, 1988, 26, 289-294.

Costa, R.A., "Photodynamic therapy with indocyanine green for occult subfoveal choroidal neovascularization caused by age-related macular degeneration," *Curr. Eye Res.*, 2001, 23(4), 271-275.

Costes, F., et al., "Comparison of muscle near-infrared spectroscopy and femoral blood gases during steady-state exercise in humans," *J. Appl. Physiol.*, 1996, 80, 1345-1350.

Coutier, S., et al., "Effect of irradiation fluence rate on the efficacy of photodynamic therapy and tumor oxygenation in meta-tetra (hydroxyphenyl) chlorine(mTHPC)-sensitized HT29 xenografts in nude mice," *Radiation Res.*, 2002, 158, 339-345.

Cubeddu, R., et al., "Time-resolved imaging on a realistic tissue phantom: $\mu_s$' and $\mu a$' images versus time-integrated images," *Appl. Opt.*, 1996, 35(22), 4533-4540.

Culver, J.P., et al., "Diffuse optical measurement of hemoglobin and cerebral blood flow in rat brain during hypercapnia, hypoxia and cardiac arrest," *Oxygen Trans. to Tissue* vol. Xxiii, 2003, 510, 293-297.

Culver, J.P., et al., "Diffuse of optical tomography of cerebral blood flow, oxygenation, and metabolism in rat during focal ischemia," *J. of Cerebral Blood Flow & Metabolism*, 2003, 23, 911-924.

Culver, J.P., et al., "Three-dimensional diffuse optical tomography in the plane parallel transmission geometry: evaluation of a hybrid frequency domain/continuous wave clinical system for breast imaging," *Med. Phys.*, 2003, 30(2), 235-247.

Danen, R.M., et al., "Regional imager for low-resolution functional imaging of the brain with diffusing near-infrared light," *Photochem. & Photobio.*, 1998, 67(1), 33-40.

De Blasi, R.A., et al., "Noninvasive measurement of human forearm oxygen consumption by near infrared spectroscopy," *Eur. J. Appl. Physiol.*, 1993, 67, 20-25.

De Blasi, R.A., et al., "Cerebral and muscle oxygen saturation measurement by frequency-domain near-infra-red spectrometer," *Med. & Biol. Eng. Comput.*, 1995, 33, 228-230.

De Blasi, R.A., et al., "Noninvasive measurement of forearm blood flow and oxygen consumption by near-infrared spectroscopy," *J. Appl. Physiol.*, 1994, 76, 1388-1393.

Delpy, D.T., et al., "Estimation of optical pathlength through tissue from direct time of flight measurement," *Phy. Med. Biol.*, 1988, 33(12), 1433-1442.

Dereski, M.O., et al., "Depth measurements and histopathological characterization of photodynamic therapy generated normal brain necrosis as a function of incident optical energy dose," *Photochem. & Phtotbio.*, 1991, 54(1), 109-112.

Detre, J.A., et al., "Perfusion magnetic resonance imaging with continous arterial spin labeling: methods and clinical applications in the central nervous system," *Eur. J. of Radiology*, 1999, 30, 115-124.

Detre, J.A., et al., "Tissue specific perfusion imaging using arterial spin labeling," *NMR in Biomedicine*, 1994, 7, 75-82.

Devaux, B.C., et al., "Experimental and clinical standards, and evolution of lasers in neurosurgery," *Acta Neurochirurgica*, 1996, 138, 1135-1147.

Dickey, D., et al., "Radiance modeling using the P3 approximation," *Physics in Med. & Biol.*, 1998, 43, 3559-3570.

Dings, J., et al., "Clinical experience with 118 brain tissue oxygen partial pressure catheter probes," *Neurosurgery*, 1998, 43(5), 1082-1094, downloaded Jul. 11, 2005, http://gateway.ut.ovid.com, 24 pages.

Dougherty, T., et al., "Photodynamic therapy," *J. Natl. Cancer Inst.*, 1998, 90(12), 889-905.

Duncan, A., et al., "Optical pathlength measurements on adult head, calf and forearm and the head of the newborn infant using phase resolved optical spectroscopy," *Phys. Med. Biol.*, 1995, 40, 295-304.

Dunn, A.K., et al., "Dynamic imaging of cerebral blood flow using laser speckle," *J. Cereb. Blood Flow Metab.*, 2001, 21, 195-201.

Durduran, T., et al., "Diffuse optical measurements of blood flow, blood oxygenation and metabolism in human brain during sensorimotor cortex activation," *Optics Letts.*, 2004, 29(15), 1766-1768.

Durduran, T., Non-Invasive Measurements of Tissue Hemodynamics with Hybrid Defense Optical Methods, *Univ. of Penn.*, 2004, Abstract. viii-xxi.

Durduran, T., et al., "Bulk optical properties of healthy female breast tissue," *Physics Medicine & Biology*, 2002, 47, 2847-2861.

Eichler, J., et al., "Temperature distribution for combined laser hyperthermia-photodynamic therapy in the esophagus," *Med. Eng. & Physics*, 2000, 22, 307-312.

Engelke, K.A., et al., "Contribution of nitric oxide and prostaglandins to reactive hyperemia in human forearm," *J. Appl. Physiol.*, 1996, 81, 1807-1814.

Fantini, S., et al., "Frequency domain multi-source optical spectrometer and oximeter," *Proc. SPIE*, 1994, 2326, 108-116.

Fantini, S., et al., "Frequency-domain optical mammography: edge effect corrections," *Med. Phys.*, 1996, 23(1), 149-157.

Fantini, S., et al., "Non-invasive optical monitoring of the newborn piglet brain using continuous-wave and frequency-domain spectroscopy," *Phys. Med. Biol.*, 1999, 44, 1543-1563.

Farrell, T.J., et al., "A diffusion theory model of spatially resolved, steady state diffuse reflectance for the noninvasive determination of tissue optical properties in vivo," *Am. Medical Physics*, 1992, 19(4), 879-888.

Farrell, T.J., et al., "Influence of layered tissue architecture on estimates of tissue optical properties obtained from spatially resolved diffuse reflectometry," *Appl. Opt.*, 1998, 37(10), 1958-1972.

Farrell, T.J., et al., "Comparison of the in vivo photodynamic threshold does for photofrin, mono- and tetrasulfonated aluminum phthalocyanine using a rat liver model," *Photochem & Photobiol*, 1998, 68(3), 394-399.

Ferrari, M., et al., "Oxidative metabolism muscles," *Philos Trans. R. Soc. Lond. B. Biol. Sci.*, 1997, 352(1354), 677-683.

Ferrari, M., et al., "Time-resolved spectroscopy of the human forearm," *J. Photochem. Photobiol B: Biol.*, 1992, 16, 141-153.

Fishkin, J., et al., "Frequency-domain method for measuring spectral properties in multiple-scattering media—methemoglobin absorption-spectrum in a tissuelike phantom," *Applied Optics*, 1995, 34(7), 1143-1155.

Flock, S.T., et al., "Optical properties of intralipid: a phantom medium for light propagation studies," *Lasers in Surgery & Medicine*, 1992, 12, 510-519.

Foster, T.H., et al., "Fluence rate effects in photodynamic therapy of multicell tumor spheroids," *Cancer Res.*, 1993, 53, 1249-1254.

Frackowiak, R.S., et al., "Quantitative measurement of regional cerebral blood flow and oxygen metabolism in man using $^{15}O$ and positron emission tomography: theory, procedure, and normal values," *J. Comput. Assit. Tomogr.*, 1980, 4, 727-736.

Franceschini, M.A., et al., "On-line optical imaging of the human brain with 160-ms temporal resolution," *Optics Express*, 2000, 6(3), 49-57.

Franceschini, M.A., et al., "Frequency-domain techniques enhance optical mammography: initial clinical results," *Proceed. of the Nat. Acad. of Sci. of the USA*, 1997, 94(12), 6468-6473.

Franceschini, M.A., et al., "Noninvasive optical method to measure tissue and arterial saturation: An application to absolute pulse oximetry of the brain," *Opt. Lett.*, 1999, 24(12), 829-831.

Franceschini, M.A., et al., "Hemodynamic evoked response of the sensorimotor cortex measured noninvasively with near-infrared optical imaging," *Psychophysiol.*, 2003, 40(4), 548-560, http://www.blackwell.synergy.com, 16 pages.

Frank, L.R., et al., "Dynamic imaging of perfusion in human skeletal muscle during exercise with arterial spin labeling," *Magn. Reson. Med.*, 1999, 42, 258-267.

Friston, K.J., et al., "Nonlinear responses in fMRI: the balloon model, volterra kennels, and other hemodynamics," *Neuroimage*, 2000, 12, 466-477.

Furutsu, K., et al., "Diffusion equation derived from the space-time transport equation," *J. Opt. Soc. Am. A*, 1980, 70(4), 360-366.

Georgakoudi, I., et al., "Singlet oxygen- versus nonsinglet oxygen-mediated mechanisms of sensitizer photobleaching and their effects on photodynamic dosimetry," *Photochem. & Photobiol.*, 1998, 67(6), 612-625.

Georgakoudi, I., et al., "The mechanism of photofrin photobleaching and its consequences for photodynamic dosimetry," *Photochem. & Photobiol.*, 1997, 65(1), 135-144.

Gesztelyi, G., et al., "Parenchymal microvascular systems and cerebral atrophy in spontaneously hypertensive rats," *Brain Res.*, 1993, 611, 249-257.

Glanzmann, T., et al., "Pharmacokinetics and pharmacodynamics of tetra($m$-hydroxphenyl)chlorine in the hamster cheek pouch tumor model: comparison with clinical measurements," *J. of Photochem. & Photobiol. B: Biology*, 2000, 57, 22-32.

Gossner, L., et al., "A new long-range through—the-scope balloon applicator for photodynamic therapy in the esophagus and cardia," *Endoscopy*, 1999, 31(5), 370-376.

Gratton, E., et al., "Measurements of scattering and absorption changes in muscle and brain," *Philosophical Trans.Biological Sciences*, 1997, 352(1354), 727-735.

Gratton, G., et al., "Fast and localized event-related optical signs (EROS) in the human occipital cortex: comparisons with the visual evoked potential and fMRI," *NeuroImage*, 1997, 6, 168-180.

Griffin, G.M., et al., "Preclinical evaluation of motexafin lutetium-mediated intraperitoneal photodynamic therapy in a canine model," *Clin. Can. Res.*, 2001, 7, 374-381.

Grinvald, A., et al., "Optical imaging of neuronal activity," *Physiological Rev.*, 1988, 68(4), 1285-1366.

Grinvald, A., et al., "Functional architecture of cortex revealed by optical imaging of intrinsic signals," *Nature*, 1986, 324, 361-364.

Groenhuis, R.A., et al., "Scattering and absorption of turbid materials determined from reflection measurements," 1. Theory, *Applied Optics*, 1983, 22(16), 2456-2462.

Grosenick, D., et al., "Development of a time-domain optical mammography and first in vivo applications," *Applied Optics*, 1999, 38(13), 2927-2943.

Grosjean, P., et al., "Clinical photodynamic therapy for superficial cancer in the oesophagus and the bronchi: 514 nm compared with 630 nm light irradiation after sensitization with photofrin II," *British J. of Cancer*, 1998, 77(11), 1989-1995.

Hahn, S., et al., "Phase I trial of motexafin lutetium-mediated photodynamic therapy in patients with locally recurrent prostate cancer," Onc Annual Meeting, 2002, Abstract 2475; http://www.asco.org, 4 pages.

Hebden, J.C., "Advances in optical imaging of the newborn infant brain," *Psychophysiol*, 2003, 40, 501-510.

Hebden, J.C., "The spatial-resolution performance of a time resolved optical imaging system using temporal extrapolation," *Med. Phys.*, 1995, 22(2), 201-208.

Heckmeier, M., et al., Imaging of dynamic heterogeneities in multiple-scattering media, *J. of the Optical Soc. of Am. A*, 1997, 14(1), 185-191.

Hellem, S., et al., "Measurements of microvascular blood flow in cancellous bone using laser Doppler flowmetry and 133Xe-clearance," *Int. J. Oral Surg.*, 1983, 12, 165-177.

Hillman, E.M.C., et al., "Time resolved optical tomography of the human forearm," *Phys. Med. Biol.*, 2001, 46, 1117-1130.

Hoge, R.D., et al., "Investigation of BOLD signal dependence on cerebral blood flow and oxygen consumption: the deoxyhemoglobin dilution model," *Magn. Reson. Med.*, 1999, 42(5), 849-863.

Hoge, R.D., et al., "Linear coupling between cerebral blood flow and oxygen consumption in activated human cortex," *Proc. Natl. Acad. Sci. USA*, 1999, 96(16), 9403-9408.

Holboke, M.J., et al., "Three-dimensional diffuse optical mammography with ultrasound localization in a human subject," *J. of Biomedical Optics*, 2000, 5(2), 237-247.

Homma, S., et al., "Near-infrared estimation of $O_2$ supply and consumption in forearm muscles working at varying intensity," *J. Appl. Physiol.*, 1996, 80, 1279-1284.

Hornung, R., et al., "Minimally-invasive debulking of ovarian cancer in the rat pelvis by means of photodynamic therapy using the pegylated photosensitizer PEG-m-THPC," *British J. of Cancer*, 1999, 81(4), 631-637.

Hsi, R.A., et al., "Photodynamic therapy in the canine prostate using motexafin lutetium," *Clin. Can. Res.*, 2001, 7, 651-660.

Hueber, D.M., et al., "Non-invasive and quantitative near-infrared haemoglobin spectrometry in the piglet brain during hypoxic stress, using a frequency-domain multidistance instrument," *Phys. Med. Biol.*, 2001, 46, 41-62.

Hull, E.L., et al., "Quantitative broadband near-infrared spectroscopy of tissue-simulating phantoms containing erthrocytes," *Phy. Med. Bio.*, 1998, 43, 3381-3404.

Hyder, F., et al., "A model for the regulation of cerebral oxygen delivery," *J. Appl. Physiol.*, 1998, 85, 554-564.

Ishimaru, A., *Wave Propagation and Scattering in Random Media*, Academic Press, Inc., 1978, vol. 2, Table of Contents, vii-xi.

Jacques, S.L., "Time-resolved reflectance spectroscopy in turbid tissues," *IEEE Trans. on Biom. Eng.*, 1989, 36(12), 1155-1161.

Jasper, H.H., "Report of the committee on methods of clinical examination in electroencephalography," *Clin. Neurophysiol.*, 1958, 10, 370-375.

Ji, Y., et al., "Toxicity of photodynamic therapy with photofrin in the normal rat brain," *Lasers in Surgery & Medicine*, 1994, 14, 219-228.

Jiang, H., et al., "Frequency-domain optical image reconstruction in turbid media: an experimental study of single-target detectability," *Applied Optics*, 1997, 36(1), 52-63.

Jiang, H., et al., "Three-dimensional optical tomographic imaging of breast in a human subject," *IEEE Trans. on Med. Imag.*, 2001, 20(12), 1334-1340.

Joannides, R., et al., "Nitric oxide is responsible for flow-dependent dilation of human peripheral conduit arteries in vivo," *Circulation*, 1995, 91, 1314-1319, http://circ.ahajournals.org, 21 pages.

Johnson, C.C., "Optical diffusion in blood," *IEEE Trans. on Biomed. Eng.*, 1970, BME17(2), 129-133.

Jones, L.R., et al., "Effects of photofrin on in vivo skin reflectivity," *J. of Photochem. & Photobiol. B-Biology*, 1996, 33, 153-156.

Jori, G., "Tumour photosensitizers: approaches to enhance the selectivity and efficiency of photodynamic therapy," *J. of Photchem. & Photobiol. B-Biology*, 1996, 36, 87-93.

Kang, K.A., et al., "Breast tumor characterization using near-infrared spectroscopy," *SPIE Proc.*, Bellingham, WA, 1993, vol. 1888, 487-499.

Kastrup, A., et al., "Changes of cerebral blood flow, oxygenation, and oxidative metabolism during graded motor activation," *NeuroImage*, 2002, 15, 74-82.

Kiel, J.W., et al., "Gastric mucosal blood flow measured by laser-doppler velocimetry," *Am. J. Physiol.*, 1985, 249, G539-G545.

Kienle A., et al., "In vivo determination of the optical properties of muscle with time-resolved reflectance using a layered model," *Phys. Med. Biol.*, 1999, 44, 2689-2702.

Kim, S.G., "Quantification of relative cerebral blood flow change by flow-sensitive alternating inversion recovery (FAIR) technique: application to functional mapping," *Mag. Res. Med.*, 1995, 34, 293-301.

Kirkham, F.J., et al., "Transcranial measurement of blood velocities in the basal cerebral arteries using pulsed Doppler ultrasound: velocity as an index of flow," *Ultrasound Med. Biol.*, 1986, 12(1), 15-21.

Klabunde, R.E., et al., "Cardiovascular physiology concepts [online]," *Ohio Univ. Col. of Osteopathic Med.*, http://www.cvphysiology.com, 2004, 1 page.

Kohl, M., et al., "Optical properties of highly scattering media determined from changes in attenuation, phase, and modulation depth," *Appl. Opt.*, 1997, 36(1), 105-115.

Kooijman, H.M., et al., "Near infrared spectroscopy for noninvasive assessment of claudication," *J. Surg. Res.*, 1997, 72,1-7.

Koukourakis, M.I., et al., "Hypoxia inducible factor (HIF-1a and HIF-2a) expression in early esophageal cancer and response to photodynamic therapy and radiotherapy," *Cancer Res.*, 2001, 61, 1830-1832.

Kuebler, W.M., et al., "Noninvasive measurement of regional cerebral blood flow by near-infrared spectroscopy and indocyanine green," *J. of Cerb. Blood Flow & Metabol.*, 1998, 18, 445-456, downloaded Jun. 30, 2005, http://www.nature.com, 22 pages.

Kushi, H., et al., "Importance of metabolic monitoring systems as an early prognostic indicator in severe head injured patients," *Acta Neurochir.*, 1999, (Suppl)75, 67-68.

Lam, S., "Photodynamic therapy of lung cancer," *Seminars in Oncology*, 1994, 21(6), 15-18.

Lange, N., et al., "Photodetection of early human bladder cancer based on the fluorescence of 5-aminolaevulinic acid hexylester-induced protoporphyrin IX: a pilot study," *British J. of Cancer*, 1999, 80(1/2), 185-193.

Laughlin, M.H., "Skeletal muscle blood flow capacity role of muscle pump in exercise hyperemia," *Am. J. Physiol.*, 1987, 253, H993-H1004.

Lebon, V., et al., "Simultaneous measurement of perfusion and oxygenation changes using a multiple gradient-echo sequence: application to human muscle study," *Magn. Reson. Imaging*, 1998, 16(7), 721-729.

Lee, L.K., et al., "Interstitial photodynamic therapy in the canine prostate," *Brit. J. of Urology*, 1997, 80, 898-902.

Lee, L.K., et al., "An interstitial light assembly for photodynamic therapy in prostatic carcinoma," *BJU International*, 1999, 84, 821-826.

Li, X., et al., "Tumor localization using fluorescence of indocyanine green (ICG) in rat model," *SPIE Proc.*, 1995, 2389, 789-797.

Li, XP., et al., "Near-field diffraction tomography with diffuse photon density waves," *Phys. Rev. E*, 2000, 61(4), 4295-4309.

Libonati, J.R., et al., "Brief muscle hypoperfusion/hyperemia: an ergogenic aid?," *J. Strength & Cond. Res.*, 2001, 15(3), 362-366.

Lilge, L., et al., "The sensitivity of the normal brain and intracranially implanted VX2 tumour to intestinal photodynamic therapy," *Br. J. Cancer*, 1996, 73, 332-343.

Mackintosh, F.C., et al., "Diffusing-wave spectroscopy and multiple scattering of light in correlated random media," *Phys. Rev. B*, 1989, 40(4), 2383-2406.

Magatti, D., et al., "25 ns software correlator for photon and fluorescence correlation spectroscopy," *Rev. Sci. Inst.*, 2003, 74(2), 1135-1144.

Magatti, D., et al., "Fast multi-tau real-time software correlator for dynamic light scattering," *Appl. Opt.*, 2001, 40(24), 4011-4021.

Maier, A., et al., "In vivo determination of tumor optical parameters in esophageal carcinoma," *Lasers in Surgery & Medicine*, 2000, 27, 350-357.

Maki, A., et al., "Spatial and temporal analysis of human motor activity using noninvasive NIR topography," *Med. Phys.*, 1995, 22(12), 1997-2005.

Maki, A., et al., "Visualizing human motor activity by using noninvasive optical topography," *Front. Med. Biol. Eng.*, 1996, 7(4), 285-297.

Mandeville, J.R., et al., "MRI measurement of the temporal evolution of relative CMRO(2) during rat forepaw stimulation," *Magn. Reson. Med.*, 1999, 42, 944-951.

Maret, G., et al., "Multiple light-scattering from disordered media. The effect of Brownian-motion of scattered Z," *Phys. B,—Condensed Matter,*, 1987, 6, 409-413.

Marijnissen, J.P., et al., "Pilot study on light dosimetry for endobronchial photodynamic therapy," *Photochem. & Photobiol.*, 1993, 58(1), 92-99.

Marijnissen, J.P., et al., "In situ light dosimetry during whole bladder wall photodynamic therapy: clinical results and experimental verification," *Physics in Med. & Biology*, 1993, 38, 567-582.

Matcher, S.J., et al., "In vivo measurements of the wavelength dependence of tissue-scattering coefficients between 760 and 900 nm measured with time-resolved spectroscopy," *Applied Optics*, 1997, 36(1), 386-396.

Mayhew, J., et al., "Spectroscopic analysis of neural activity in brain: increased oxygen consumption following activation of barrel cortex," *Neuroimage*, 2000, 12, 664-675.

Mayhew, J., et al., "Increased oxygen consumption following activation of brain: theoretical footnotes using spectroscopic data from barrel cortex," *Neuroimage*, 2001, 13, 975-987.

McBride, T.O., et al., "Multispectral near-infrared tomography: a case study in compensating for water and lipid content in hemoglobin imaging of the breast," *J. of Biom. Opt.*, 2002, 7(1), 72-79.

Mehagnoul-Schipper, D.J., et al., "Simultaneous measurements of cerebral oxygenation changes during brain activation by near-infrared spectroscopy and functional magnetic resonance imaging in healthy young and elderly subjects," *Human Brain Mapping*, 2002, 16, 14-23.

Menon, C., et al., "An integrated approach to measuring tumor oxygen status using human melanoma xenografts as a model," *Cancer Res.*, 2003, 63, 7232-7240.

Miller, E., "Focus issue: diffuse optical tomography-introduction," *Optics Express*, 2000, 7(13), p. 461.

Mitra, S., et al., "Photochemical oxygen consumption sensitized by porphyrin phosphorescent probe in two model systems," *Biophysical J.*, 2000, 78, 2597-2605.

Miura, H., et al., "Regional difference of muscle oxygen saturation and blood volume during exercise determined by near infrared imaging device," *Jap. J. of Physiology*, 2001, 51, 599-606.

Mohler, E.R., "Peripheral arterial disease," *Curr. Treat. Options Cardiovasc Med. 1*, 1999, 27-34.

Mohler, E.R., "Peripheral arterial disease: identification and implications," *Arch. Intern. Med.*, 2003, 163, 2306-2314.

Morton, C.A., et al., "Camparison of red and green light in the treatment of Bowen's disease by photodynamic therapy," *British J. of Dermatology*, 2000, 143, 767-772.

Muellner, T., et al., "New instrument that uses near-infrared spectroscopy for the monitoring of human muscle oxygenation," *J. Trauma*, 1999, 46(6), 1082-1084, http://gateway.ut.ovid.com, 7 pages.

Nathan, T.R., et al., "Photodynamic therapy for prostate cancer recurrence after radiotherapy: a phase I study," *J. of Urology*, 2002, 168(4, part 1 of 2), 1427-1432, http://gateway.ut.ovid.com, 9 pages.

Newman, M.F., et al., "Longitudinal assessment of neurocognitive function after coronary-artery bypass surgery," *N. Engl. J. Med.*, 2001, 344, 395-402.

Nichols, M.G., et al., "Oxygen diffusion and reaction kinetics in the photodynamic therapy of multicell tumour spheroids," *Phys. Med. Biol.*, 1994, 39, 2161-2181.

Nichols, M.G., et al., "Microelectrode measurements of photochemical oxygen depletion in multicell tumor spheroids during photodynamic therapy," prepublishing for SPIE 1994.

Nioka, S., et al., "Muscle deoxygenation in aerobic and anaerobic exercise," *Adv. Exp. Med. Boil.*, 1998, Chapter 8, 454, 63-70.

Nioka, S., et al., "Optical imaging of human breast cancer," *Adv. Exp. Med. Biol.*, 1994, 361, 171-179.

Nioka, S., et al., "Human brain functional imaging with reflectance CWS," *Oxygen Trans. to Tissue Xix*, 1997, Chapter 33, 428, 237-242.

Ntziachristos, V., et al., "Concurrent MRI and diffuse optical tomography of breast after indocyanine green enhancement," *Proc. of the Nat. Acad. of Sci. of the USA*, 2000, 97(6), 2767-2772.

Ntziachristos, V., et al., "Probing physiology and molecular function using optical imaging: applications to breast cancer," *Breast Cancer Res.*, 2001, 3, 41-46.

Ntziachristos, V., et al., "MRI-guided diffuse optical spectroscopy of malignant and benign breast lesions," *Neoplasia* (NY), 2002, 4(4), 347-354.

Ntziachristos, V., et al., "Comparison between intrinsic and extrinsic contrast for malignancy detection using NIR mammography," *Proceedings of Optical Tomography & Spectroscopy of Tissue, III*, 1999, 565-570.

Ntziachristos, V., et al., "Multichannel photon counting instrument for spatially resolved near infrared spectroscopy," *Rev. of Scientific Instruments*, 1999, 70(1), 193-201.

Oberg, P.A., et al., "Use of a new laser Doppler flowmeter for measurements of capillary blood flow in skeletal muscle after bullet wounding," *Acta Chir. Scand. Suppl.*, 1979, 489, 145-150.

Okada, E., et al., "Near-infrared light propagation in an adult head model. II. Effect of superficial tissue thickness on the sensitivity of the near-infrared spectroscopy signal," *Appl. Opt.*, 2003, 42(16), 2915-2922.

Obrig, H., et al., "Near-infrared spectroscopy in functional activation studies. Can NIRS demonstrate cortical activation," *Adv. Exp. Med. Biol.*, 1997, Chapter 13, 413, 113-127.

O'Leary, M.A., et al., "Fluorescence lifetime imaging in turbid media," reprint from *Optics Letts.*, 1996, 21(2), 158-160.

O'Leary, M.A., et al., "Experimental images of heterogeneous turbid media by frequency-domain diffusing-photon tomography," *Optics Letts.*, 1995, 20(5), 426-428.

Ornstein, D.K., et al., "Evaluation and management of men whose radical prostatectomies failed: results of an international survey," *Urology*, 1998, 1047-1054.

Orth, K., et al., "Fluorescence detection of small gastrointestinal tumours: principles, technique, first clinical experience," *Langenbecks Archives of Surgery*, 2000, 385, 488-494.

Pantelides, M.L., et al., "Photodynamic therapy for localized prostatic cancer. Light penetration in the human prostate gland," *J. of Urology*, 1990, 143, 398-401.

Patterson, M.S., et al., "Frequency-domain reflectance for the determination of the scattering and absorption properties of tissue," *Appl. Opt.*, 1991, 30(31), 4474-4476.

Patterson, M.S., et al., "Time resolved reflectance and transmittance for the non-invasive measurement of tissue optical properties," *Applied Optics*, 1989, 28(12), 2331-2336.

Patterson, M..S., et al., "In vivo tests of the concept of photodynamic threshold does in normal rat liver photosensitized by aluminum chlorosulphonated phthalocyanine," *Photochem & Photobiol*, 1990, 51(3), 343-349.

Pham, T., et al., "Monitoring tumor response during photodynamic therapy using near-infrared photon-migration spectroscopy," *Photochem. Photobiol.*, 2001, 73(6), 669-677.

Phelps, M.E., et al., "Clinical PET—what are the issues," *J. Nucl. Med.*, 1985, 26(12), 1353-1358.

Pindzola, R.R., et al., "The xenon-enhanced computed tomography cerebral blood flow method," *Neurosurgery*, 1998, 43(6), 1488-1492, downloaded Jul. 7, 2005, http://www.gateway.ut.com, 10 pages.

Pine, D.J., et al., "Diffusing-wave spectroscopy," *Phys. Rev. Let.*, 1988, 60(12), 1134-1137.

Pogue, B.W., et al., "Frequency-domain optical-absorption spectroscopy of finite tissue volumes using diffusion-theory," *Phys. Med. Biol.*, 1994, 39, 1157-1180.

Pogue, B.W., et al., "Initial assessment of a simple system for frequency domain diffuse optical tomography," *Phys. Med. Biol.*, 1995, 40, 1709-1729.

Pogue, B.W., et al., "Instrumentation and design of a frequency-domain diffuse optical tomography imager for breast cancer detection," *Optics Express*, 1997, 1(13), 391-403.

Pogue, B.,W., et al., "High-resolution near-infrared tomographic image simulations of the rat cranium by use of a priori magnetic resonance imaging structural information," *Optic Letts.*, 1998, 23(21), 1716-1719.

Pogue, B.W., et al., "Hemoglobin imaging of breast tumors with near-infrared tomography," *Radiology*, 2000, 214, p. 609.

Pogue, B.W., et al., "Quantitative hemoglobin tomography with diffuse near-infrared spectroscopy: pilot results in the breast," *Radiology*, 2001, 218, 261-266, downloaded Jul. 7, 2005, 13 pages.

Pogue, B., et al., "Analysis of the heterogeneity of $pO_2$ dynamics during photodynamic therapy with verteporfin," *Photochem. & Photobiol.*, 2001, 74(5), 700-706.

Pogue, B.W., et al., "A theoretical study of light fractionation and dose-rate effects in photodynamic therapy," *Radiation Res.*, 1997, 147, 551-559.

Potter, W.R., et al., "The theory of photodynamic therapy dosimetry: consequences of photo-destruction of sensitizer," *Photochem. & Photobiol*, 1987, 46(1), 97-101.

Proskurin, S.G., et al., "Absorption coefficient measurements of strongly scattering media using time-resolved transmittance of a short pulse in near-infrared wavelength range," *Optical Rev.*, 1995, 2(4), 292-297.

Quaresima, V., et al., "Calf and shin muscle oxygenation patterns and femoral artery blood flow during dynamic plantar flexion exercise in humans," *Eur. J. appl. Physiol.*, 2001, 84, 387-394.

Quaresima, V., et al., "Noninvasive measurement of cerebral hemoglobin oxygen saturation using two near infrared spectroscopy approaches," *J. Biomed. Opt.*, 2000, 5(2), 201-205.

Quaresima, V., et al., "Identification and quantification of intrinsic optical contrast for near-infrared mammography," *Photochem. & Photobiol.*, 1998, 67(1), 4-14.

Raynaud, J.S., et al., "Determination of skeletal muscle perfusion using arterial spin labeling NMRI: validation by comparison with venous occlusion plethysmography," *Magn. Res. Med.*, 2001, 46, 305-311.

Reivich, M., et al., "The [18F] fluorodeoxyglucose method for the measurement of local cerebral glucose ultilization in human," *Circ. Res.*, 1979, 44, 127-137.

Reynolds, J.S., et al., "Optical diffusion imaging: a comparative numerical and experimental study," *Applied Otpics*, 1996, 35(19), 3671-3679.

Reynolds, J.S., et al., "Imaging of spontaneous canine mammary tumors using fluorescent contrast agents," *Photochem Photobiol*, 1999, 70(1), 87-94.

Richter, A.M., et al., "Photosensitizing potencies of the structural analogues of benzoporphyrin derivative in different biological test systems," *J. of Clin. Laser Med. & Surg.*, 1996, 14(5), 335-341.

Ripoll, J., et al., "Recovery of optical parameters in multiple-layered diffusive media: theory and experiments," *J. Opt. Soc. A.*, 2001, 18(4), 821-830.

Riva, C.E., et al., "Laser doppler measurements of blood flow in capillary tubes and retinal arteries," *Invest. Ophthalmol.*, 1972, 11, 936-944.

Roach, G.W., et al., "Adverse cerebral outcomes after coronary bypass surgery," *N. Engl. J. of Med.*, 1996, 335(25), 1857-1863.

Robinson, D.J., et al., "Fluorescence photobleaching of ALA-induced protoporphyrin IX during photodynamic therapy of normal hairless mouse skin: the effect of light dose and irradiance and the resulting biological effect," *Photochem. & Photobiol.*, 1998, 67(1), 140-149.

Roland, P.E., et al., "Supplementary motor area and other cortical areas in organization of voluntary movements in man," *J. Neurophysiiol*, 1980, 43, 118-136.

Rueckert, P.A., et al., "Comparison of arterial occlusion and ischaemic exercise for the study of vasodilatation in the human calf," *Clin. Sci.* (Lond.), 1995, 88, 643-649.

Rutherford, R.B., et al., "Recommended standards for reports dealing with lower extremity ischemia," revised version, *J. Vasc. Surg.*, 1997, 26, 517-538.

Sako, T., et al., "Validity of NIR spectroscopy for quantitatively measuring muscle oxidative metabolic rate in exercise," *J. Appl. Physiol.*, 2001, 90, 338-344.

Seelbach-Goebel, B., "Correlation between NIR spectroscopy and pulse oximetry in the fetus," *J. Peninat. Med.*, 1996, 24, 69-75.

Seitz, R.J., et al., "Learning of sequential finger movements in man: a combined kinematic and positron emission tomography (PET) study," *Eur. J. Neurosci.*, 1992, 4, 154-165.

Sevick, E.M., et al., "Quantitation of time- and frequency-resolved optical spectra for the determination of tissue oxygenation," *Analyt. Biochem.*, 1991, 195, 330-351.

Sevick-Muraca, E.M., et al., "Fluorescence lifetime spectroscopic imaging with measurements of photon migration," *Ann NY Acad. Sci.*, 1998, 838, 46-57.

Shackley, D.C., et al., "Light penetration in bladder tissue: implications for the intravesical photodynamic therapy of bladder tumours," *BJU International*, 2000, 86, 638-643.

Shah, N., et al., "Noninvasive functional optical spectroscopy of human breast tissue," *Proc. Natl. Acad. Sci. USA*, 2001, 98(8), 4420-4425.

Sheinberg, M., et al., "Continuous monitoring of jugular venous oxygen saturation in head-injury patients," *J. Neurosurg.*, 1992, 76, 212-217.

Shepherd, A.P., et al., "Continuous measurements of intestinal mucosal blood flow by laser-dopplier velocimetry," *Am. J. Physiol.*, 1982, 242, G668-G672.

Siegel, A.M., et al., "Design and evaluation of a continuous-wave diffuse optical tomography system," *Optics Exp.*, 1999, 4(8), 287-298.

Smith, R.J., et al., "Quantitative measurements of cerebral blood flow in volume imaging PET scanners," *IEEE Transactions on Nuclear Sci.*, 1995, 42(4), 1018-1023.

Solonenko, M., et al., "In vivo reflectance measurement of optical properties, blood oxygenation and motexafin lutetium uptake in canine large bowels, kidneys and prostates," *Physics in Medic. & Biol.*, 2002, 47, 857-873.

Stamey, T., "Iradiation as primary treatment for prostate cancer," *Am. Urol. Assoc. Today*, 1993, 6, 14.

Stångä, D., "Comments on 'problems associated with the use of broad-band illumination sources for photodynamic therapy,'" *Physics in med. & Biol.*, 1996, 41, 1517-1530.

Star, W.M., et al., "Light dosimetry in vivo," *Physics in Med. & Biol.*, 1997, 42, 763-787.

Steinbrink, J., et al., "Determining changes in NIR absorption using a layered model of the human head," *Phys. Med. Biol.*, 2001, 46, 879-896.

Stephen, M.J., "Temporal fluctuations in wave propagation in random media," *Phys. Rev. B*, 1988, 37(1), 1-5.

Stern, M.D., "In vivo evaluation of microcirculation by coherent light scattering," *Nature*, 1975, 254, 56-58.

Stern, M.D., et al., "Continuous measurements of tissue blood flow by laser-doppler spectroscopy," *Am. J. Physiol.*, 1977, 232, H441-H448.

Stern, M.D., et al., "Measurements of renal cortical and medullary blood flow by laser-doppler spectroscopy in the rat," *Am. J. Physiol.*, 1979, 236, F80-F87.

Strangman, G., et al., "Factors affecting the accuracy of near-infrared spectroscopy concentration calculations for focal changes in oxygenation parameters," *Neuroimage*, 2003, 18, 865-879.

Suzuki, K., et al., "Quantitative measurement of optical-parameters in the breast using time-resolved spectroscopy—Phantom and preliminary in-vivo results," *Investigative Radiology*, 1994, 29, 410-414.

Svaasand, L.O., et al., "Tissue characterization and imaging using photon density waves," *Optical Eng.*, 1993, 32, 258-266.

Tagawa, T., et al., "Role of nitric oxide in reactive hyperemia in human forearm vessels," *Circulation*, 1994, 90, 2285-2290.

Tanaka, T., et al., "Measurement of the velocity of blood flow (in vivo) using a fiber optic catheter and optical mixing spectroscopy," *Applied Optics*, 1975, 14(1), 189-196.

Tanaka, T., et al., "Blood velocity measurements in human retinal vessels," *Science*, 1974, 186(4166), 830-831.

Taylor, K.M., "Central nervous system effects of cardiopulmonary bypass," *Ann Thorac Surg.*, 1998, 66, S20-S24.

Tenland, T., et al., "Spatial and temporal variations in human skin blood flow," *Int. J. Microcirc. Clin. Exp.*, 1983, 2, 81-90.

Tong, P., et al., "Turbulent transition by photon-correlation spectroscopy," *Phys. Rev. A.*, 1988, 37(6), 2125-2133.

Toronov, V., et al., "Near-infrared study of fluctuation in cerebral hemodynamics during rest and motor stimulation: temporal analysis and spatial mapping," *Med. Phys.*, 2000, 27(4), 801-815.

Toussaint, J.F., et al., "Interrelationship of oxidative metabolism and local perfusion demonstrated by NMR in human skeletal muscle," *J. Appl. Physiol.*, 1996, 81, 2221-2228.

Toussaint, J.F., et al., "Perfusion changes in human skeletal muscle during reactive hyperemia measured by echo-phanar imaging," *Magn. Reson. Med.*, 1996, 33, 62-69.

Trepte, O., et al., "Studies of porphyrin-containing specimens using an optical spectrometer connected to a confocal scanning laser microscope," *J. of Microscopy*, 1994, 176(3), 238-244.

Tromberg, B.J., "Non-invasive in vivo characterization of breast tumors using photon migration spectroscopy," *Neoplasia*, 2000, 2(1-2), 26-40.

Tromberg, B.J., et al., "A mathematical model for light dosimetry in photodynamic destruction of human endometrium," *Physics in Med. & Biology*, 1996, 41, 223-237.

Tromberg, B., et al., "In vivo tumor oxygen tension measurements for the evaluation of the efficiency of photodynamic therapy," *Photochem. & Photobiol.*, 1990, 52(2), 375-385.

Tromberg, B., et al., "Diffusing photons in turbid media: introduction to the feature," *Applied Optics*, 1997, 36(1), p. 9.

Tsoukas, M.M., et al., "Predictive dosimetry for threshold phototoxicity in photodynamic therapy on normal skin: red wavelengths produce more extensive damage than blue at equal threshold doses," *J. of Investig. Dermat.*, 1997, 108, 501-505.

VaB Santbrink, H., et al., "Continuous monitoring of partial pressure of brain tissue oxygen in patients with severe head injury," *Neurosurgery*, 1996, 38(1), 21-31.

Val'kov, A.Y., et al., "Characteristics of propogation and scattering of light in nematic liquid crystals," *Sov. Phys. JETP*, 1986, 63(4), 737-743.

Van Beekvelt, M.C., et al., "Performance of near-infrared spectroscopy in measuring local O(2) consumption and blood flow in skeletal muscle," *J. Appl. Physiol.*, 2001, 90, 511-519.

Van den Bergh, H., "On the evolution of some endoscopic light delivery systems for photodynamic therapy.[comment]," *Endoscopy*, 1998, 30, 392-407.

Van der Zee, P., et al., "Experimentally measured optical pathlengths for the adult's head, calf and forearm and the head of the newborn infant as a function of inter optode spacing," *Adv. Exp. Med. Biol.*, 1992, 316, 143-153.

Van der Zee, P., et al., "Optical properties of brain tissue," *SPIE Proceedings*, 1993, 1888, 454-465.

Van Gemert, J.C., et al., "Wavelength and light dose dependence in tumor phototherapy with haematoporphyrin derivative," *Br. J. of Cancer*, 1985, 52, 43-49.

Van Hillegersberg, R., et al., "Current status of photodynamic therapy in oncology," *Drugs*, 1994, 48, 510-527.

Van Staveren, H.J., et al., "Integrating sphere effect in whole-bladder-wall photodynamic therapy: II. The influence of urine at 458, 488, 514 and 630 nm optical irradiation," *Physics in Med. & Biol.*, 1995, 40, 1307-1315.

Van Staveren, H.J., et al., "Bladder PDT with intravesical clear and light scattering media: effect of an eccentric isotroptic light source on the light distribution," *Lasers in Surg. & Med.*, 1997, 20, 248-253.

Van Staveren, H.J., et al., "Light scattering in intralipid-10% in the wavelength range of 400-1100 nm," *Applied Optics*, 1991, 30(31), 4507-4514.

Van Veen, et al., "Wedge-shaped applicator for additional ight delivery and dosimetry in the diaphragmal sinus during photodynamic therapy for malignant pleural mesothelioma," *Phys.Med. Biol.*, 2001, 46, 1873-1883.

Villringer, A., et al., "Non-invasive optical spectroscopy and imaging of human brain function," *Trends Neurosci.*, 1997, 20(10), 435-442.

Villringer, A., et al., "Near infrared spectroscopy (NIRS): a new tool to study hemodynamic changes during activation of brain function in human adults," *Neuroscience Letts.*, 1993, 154, 101-104.

Vulcan, T.G., et al., "Comparison between isotropic and nonisotropic dosimetry systems during intraperitoneal photodynamic therapy," *Lasers in Surgery and Medicine*, 2000, 26, 292-301.

Wagnieres, G., et al., "An optical phantom with tissue-like properties in the visible for use in PDT and fluorescence spectroscopy," *Physics in Med. & Biol.*, 1997, 42, 1415-1426.

Wahr, J.A., et al., "Near-infrared spectroscopy: theory and applications," *J. Cardiothoracic and Vascular Anesthesia*, 1996, 10(3), 406-418.

Walker, S.A., et al., "Photon density waves scattered from cylindrical inhomogeneities: theory and experiments," *Appl. Opts.*, 1998, 37(10), 1935-1944.

Wallace, D.J., et al., "Summary of the results of a 95-subject human clinical trial for the diagnosis of peripheral vascular disease using a near-infrared frequency domain hemoglobin spectrometer," *Proceedings of SPIE*, San Jose, CA, Chance, B., et al. (Eds.), 1999, 300-316.

Wang, J., et al., "Arterial spin labeling perfusion fMRI with very low task requency," *Magn. Reson Med.*, 2003, 49, 796-802.

Wang, H., et al., "In-vivo diffuse reflectance measurement of optical properties in human tissues before and after photodynamic therapy," *Medical Physics*, 2002, 29(6), p. 1197.

Wang, H., et al., "In vivo Measurements of penetration depth, oxygenation, and drug concentration using broadband absorption and fluorescence spectroscopy in human tissues before and after photodynamic therapy," *SPIE*, 2003, 4 pages.

Whithurst, G., et al., "Optimization of multifiber light delivery for the photodynamic therapy of localized prostate cancer," *Photochem. & Photobiol.*, 1993, 58(4), 589-593.

Whitehurst, G., et al., "In vivo laser light distribution in human prostatic carcinoma," *J. of Urology*, 1994, 151, 1411-1415.

Whitney, R.J., "The measurement of volume changes in human limbs," *J. Physiol.*, 1953, 121, 1-27.

Williams, P.C., et al., "Mapping of cerebral cortical strokes in rhesus monkeys by laser Doppler spectroscopy," *Med. Res. Eng.*, 1980, 13, 3-5.

Wilson, B.C., "Photodynamic therapy for cancer: principles," *Canadian J. of Gastroenterology*, 2002, 16(6), 393-396.

Wilson, B.C., et al., "Implicit and explicit dosimetry in photodynamic therapy: a new paradigm," *Lasers in Medical Science*, 1997, 12, 182-192.

Windahl, T., et al., Photodynamic therapy of localized prostatic cancer, *The Lancet*, 1990, 336, p. 1139.

Wolf, U., et al., "Localized irregularities in hemoglobin flow and oxygenation in calf muscle in patients with peripheral vascular disease detected with near-infrared spectrophotometry," *J. Vasc. Surg.*, 2003, 37, 1017-1026.

Wolf, U., et al., "Mapping of hemodynamics on the human calf with near infrared spectroscopy and the influence of the adipose tissue thickness," *Adv. Exp. Med. Biol.*, 2003, 510, 225-230.

Wray, S., et al., "Characteristics of the near infrared absorption spectra of cytochrome $aa_3$ and hemoglobin for the noninvasive monitoring of cerebral oxygenation," *Biochim. Biophys Acta*, 1988, 933, 184-192.

Wyatt, J.S., et al., "Quantification of cerebral oxygenation and haemodynamics in sick newborn infants by near infrared spectrophotometry," *The Lancet*, 1986, 1063-1066.

Wyss, P., et al., "Photomedicine of the endometrium: experimental concepts," *Human Reproduction*, 1995, 10(1), 221-226.

Xu, Y., et al., "Imaging of in vitro and in vivo bones and joints with continuous-wave diffuse optical tomography," *Optics Express*, 2001, 8, 447-451.

Ye, F.Q., et al., "Quantitation of regional cerebral blood flow increases during motor activation: a multislice, steady-state, arterial spin tagging study," *Mag. Res. in Med.*, 1999, 42, 404-407.

Yodh, A.G., et al., "Functional imaging with diffusing light," *Biomedical Photonics Handbook*, CRC Press, 2003, Chapter: 21-1-21-45.

Yodh, A., et al., "Spectroscopy and imaging with diffusing light," *Physics Today*, 1995, 48, 34-40.

Yonas, R.P., et al., "Xenon/computed tomography cerebral blood flow and its use in clinical management," *Neurosurg. Clin. N. Am.*, 1996, 7(4), 605-616.

Yoshida, T., et al., "Clinical study of photodynamic therapy for laryngeal cancer," *Nippon Jibinkoka Gakkai Kaiho* [*J. of the Oto-Rino-Laryngological Soc. of Japan*], 1995, 98, 795-804 (English Abstract).

Yu, G., et al., "Non-invasive monitoring of hemodynamic responses in RIF tumors during and after PDT," *Proceedings of SPIE Photonics*, Kessel, D., et al. (Eds.), 2003, 4952, 131-139.

Yu, G., et al., "Frequency-domain multiplexing system for in vivo diffuse light measurements of rapid cerebral hemodynamics," *Applied Optics*, 2003, 42(16), 2931-2939.

Yu, G., et al., Noninvasive monitoring of murine tumor blood flow during and after photodynamic therapy provides early assessment of therapeutic efficacy, *Clin. Cancer Res.*, 2005, 11(9), 3543-3552.

Yu, G., et al., "Time-dependent blood flow and oxygenation in human skeletal muscles measured with noninvasive near-infrared diffuse optical spectroscopies," *J. of Biomedical Optics*, 2005, 10(2), 024027-1-024027-12.

Zheng, Y., et al., "A model of the hemodynamic response and oxygen delivery to brain," *Neuroimage*, 2002, 16, 617-637.

Zhu, Q., et al., "Imager that combines near-infrared diffusive light and ultrasound," *Optics Letts.*, 1999, 24(15), 1050-1052.

Zhu, Q., et al., "Optical imaging as an adjunct to sonograph in differentiating benign from malignant breast lesions," *J. Biomed. Opt.*, 2000, 5(2), 229-236.

Zhu, T., et al., "In vivo optical properties of normal canine prostate at 732 nm using motexafin lutetium-mediated photodynamic therapy," *Photochem. & Photobiol.*, 2003, 77(1), 81-88.

\* cited by examiner

OPTICAL MEASUREMENT OF TISSUE BLOOD FLOW, HEMODYNAMICS AND OXYGENATION

CROSS-REFERENCE TO RELATED CASES

This application claims priority under 35 U.S.C. §119(e) from U.S. Provisional Application Ser. No. 60/561,758 filed on Apr. 13, 2004, entitled "Diffuse Correlation Methods For Measurement Of Cerebral Blood Flow In Man" which is herein incorporated by reference in its entirety.

FIELD OF THE INVENTION

The invention relates generally to the measurement of blood flow, oxy- and/deoxy hemoglobins, and oxygenation, scattering and hemodynamic characteristics in tissue. More specifically, the invention relates to methods and apparatus for measuring the flow of blood and oxygenation characteristics using diffuse optical spectroscopy and imaging and diffuse correlation methods.

BACKGROUND OF THE INVENTION

In the late 1970s, dynamic light scattering theory was applied to living tissue to measure blood flow. Multiple scattering from the blood occurred, resulting for example, in a Doppler broadening of the indirect laser linewidth. In the early 1980s, a theory for how to use diffuse light to measure motional fluctuations in turbid media was discovered. The theory was termed "diffusing wave spectroscopy."

Diffusing wave spectroscopy enabled a range of dynamical studies of optically dense systems in which scattering particles are moving. However, in these systems, the medium generally was homogeneous in that there were no spatial variations in the dynamic or optical properties. Therefore, these techniques for measuring motions with diffuse light were limited because they could not characterize media with spatially varying, dynamic properties.

Overtime diffuse imaging and spectroscopy techniques evolved to permit measurement and imaging heterogeneous media such as tissue. The method could be applied to tumors, burns, and other real world structures found in the human body. Such techniques are discussed in detail in U.S. Pat. No. 6,076,010, which is herein incorporated by reference in its entirety. Specifically, these techniques irradiate the medium with a source of light that diffuses through the medium. A measurement is taken of the temporal intensity fluctuations of photon streams that have been scattered within the medium. The medium's properties, for example blood flow rate, are then determined using measured temporal correlation functions of the diffuse light (for example as a function of placement on the tissue surface). We will refer to the methodology as diffuse correlation spectroscopy (DCS).

Various other methods for measuring blood flow have been developed and employed. For example, conventional venous occlusion plethysmography has been employed for more than fifty years in muscle perfusion investigations. However, this method does not provide regional information and can be used only in the static state, during functional activation, or during brief exercise because it interrupts blood flow. Also, ultrasound Doppler techniques are a common clinical tool used to measure blood flow in large vessels. However, the Doppler techniques are not very sensitive to blood flow in smaller vessels, and do not readily permit continuous measurements during exercise. Laser Doppler techniques also have been used more recently, but typically they only measure the tissue surface. Magnetic resonance imaging (MRI) has high temporal and spatial resolution, and has become a gold standard technique for noninvasive measurement of blood flow and metabolic response. However, MRI's clinical use is limited due to high cost and poor mobility, and it's function form has poor sensitivity.

Diffuse correlation spectroscopy (DCS) is an emerging technique for continuous measurement of relative blood flow non-invasively in deep tissues. It has been successfully applied in studies of brain hemodynamics, PDT dosimetry and for measurement of burn depth. DCS enables measurements of relative blood flow (rBF) with high temporal and low spatial resolution in tissue. To date most (but not all) applications of DCS have been in small animal studies wherein source-detector separations were comparatively small. Discussion of DCS techniques has been described in U.S. Pat. No. 6,076,010, which is incorporated herein by reference in its entirety.

Combining these blood flow rate determinations with oxygenation and hemodynamic tissue properties determined by diffused optical spectroscopy or characteristics further facilitates the understanding of vascular conditions and tissue metabolism, as well as for example in peripheral arterial disease (PAD). In general these improved measurements will enable improved screening of tissues and treatment assessment, as well as to improved fundamental understanding of tissue function. Therefore, there is a real value in such noninvasive optical techniques for study of blood flow, hemodynamics and oxygenation in tissue.

SUMMARY OF THE INVENTION

An embodiment of the invention includes a device, system and method for determining the characteristics of deep tissue. The novel method includes measuring blood flow rate, hemodynamics and oxygenation characteristics of the tissue, and for determining oxygen metabolism or changes thereof of the tissue. The blood flow rate characteristics are measured by monitoring light fluctuations caused by motions within the tissue, (e.g. blood flow) while the hemodynamics and blood oxygenation characteristics are measured by the transmission of light through the tissue, e.g. with respect to the wavelength of light. The tissue may be layered tissue, for example, a portion of a brain. The tissue characteristics may be measured during times of varying levels of exercise intensity. Also, the invented method may conduct measurement of the autocorrelation function of the transmitted light. The inventive method further may comprise determining an extent of the movement of a blood cell in the tissue, and/or determining the velocity of the movement of a blood cell in the tissue. Also, the blood flow rate, hemodynamics and oxygenation are measured substantially simultaneously. The inventive method may be used to monitor peripheral vascular disease, tumor response, brain activation and/or to determine the efficacy of a drug used to facilitate blood flow.

DETAILED DESCRIPTION OF ILLUSTRATIVE EMBODIMENTS

Figure 1:
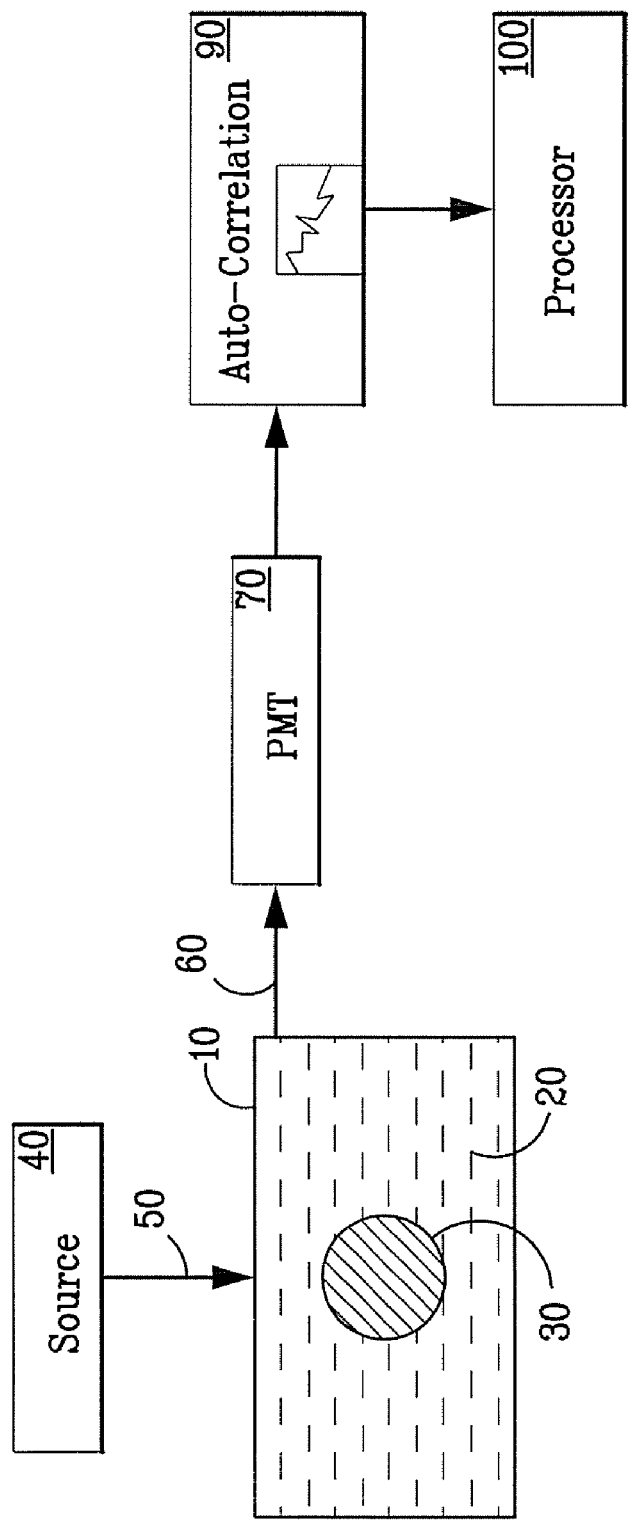
FIG. 1 is a block diagram of a system for imaging turbid media with spatially varying dynamic properties or spatially varying optical properties provided in accordance with the present invention.

Referring now to the drawings wherein like reference numerals refer to like elements, FIG. 1 is a block diagram of a system provided in accordance with the present invention for imaging media having spatially varying dynamic properties or spatially varying optical properties.

A turbid medium is shown generally at 10, and comprises a substantially heterogeneous matrix 20 wherein there is embedded an object 30. The object 30 contains small particles which are moving in a non-ordered fashion. "Non-ordered fashion" means that the particles exhibit Brownian motion, turbulent motion, shear flow, random motion, velocity changes or any other motion which results in a change in the relative distance between the particles. This is what is meant by the term "dynamic" throughout. In practice the background medium could also be "dynamic." In an experimental setup which has been used to verify the systems of the present invention, the matrix 20 is a solid slab of titanium dioxide suspended in resin, and the object 30 is a small cavity with a 0.2 percent suspension of 0.296 micrometer diameter polystyrene spheres. The slab has dimensions of 15.times.15.times.8 centimeters.

A source of light 40 is coupled by a multimode fiber 50 to the medium 10. Preferably, the source 40 is a coherent source of energy. Even more preferably, the source is a laser or a stable light source, well known to those skilled in the art. Most preferably, the source is an argon ion laser which outputs energy in the 514 nanometer green wavelength range.

A fiber 60 is placed at a known position with respect to the matrix 20, and will pick up light which diffuses through the medium 10. A detector 70 is interfaced to the fiber, and by standard gain techniques creates a signal which is representative of the intensity fluctuations at the fiber resulting from the photons which have diffused through the medium 10 and which may have scattered from the particles in object 30. Any detector which can produce a gain, for example a photomultiplier tube, can be interfaced with the fiber 60, and it will be recognized by those with skill in the art that a fiber-detector combination will produce the results required in accordance with the invention. A preferred embodiment of fiber 60 is a single mode fiber.

In accordance with the present invention, a digital autocorrelator 90 is interfaced with the photomultiplier tube 70 in order to observe the intensity fluctuations of the signal speckle. The digital autocorrelation device 90, which is a well-known electronic system that is commercially available, measures the temporal intensity autocorrelation function of the photons received by the detector. As will be described in more detail below, this autocorrelation function can be used to obtain the scattering, absorption and dynamic characteristics of the medium in accordance with the methodology described herein.

In accordance with the invention, autocorrelation functions are measured with the source and collecting fibers individually positioned at different locations with respect to the object 30. A computer processor 100 with the appropriate software that implements the correlation diffusion theory described below determines the scattering, absorption and dynamic characteristics of the medium from the diffusion correlation wave and thereby reconstructs an image of the dynamically heterogeneous medium 10. Also, the computer may include software that allows a calculation of a correlation function. The computer can be any known, standard processor which can utilize the correlation information output by the autocorrelator 90. In this manner, a reconstructed image of the medium 10 having the object 30 therein can be produced as a function of the scattering and absorption of the diffuse correlation wave as it propagates diffusing through the medium 10.

It has been demonstrated that transmission and remission measurements of diffuse light intensity emerging from heterogeneous turbid media can provide adequate information for the construction of low resolution images of the spatially varying absorption and scattering coefficients. When the medium is dynamic, the time-dependent density fluctuations of the sample are impressed upon the temporal behavior of the diffusing light. For homogeneous fluctuating turbid media, the temporal intensity autocorrelation function of an emerging speckle of diffuse light can be analyzed to provide information about the temporal fluctuations within the sample. This is the technique we will refer to as diffuse correlation spectroscopy. Just as diffuse photon density waves can be used to probe the spatial variations in absorption and scattering coefficients within heterogeneous media, position-dependent measurements of the temporal autocorrelation function of diffusing light fields can be used to generate images of temporal fluctuations within heterogeneous turbid media. The techniques of the present invention provide a new contrast mechanism for imaging within turbid media. Specifically, these techniques can distinguish regions of strong and weak density fluctuations such as calcium deposits versus soft tissue or blood flow versus stasis.

Figure 2:
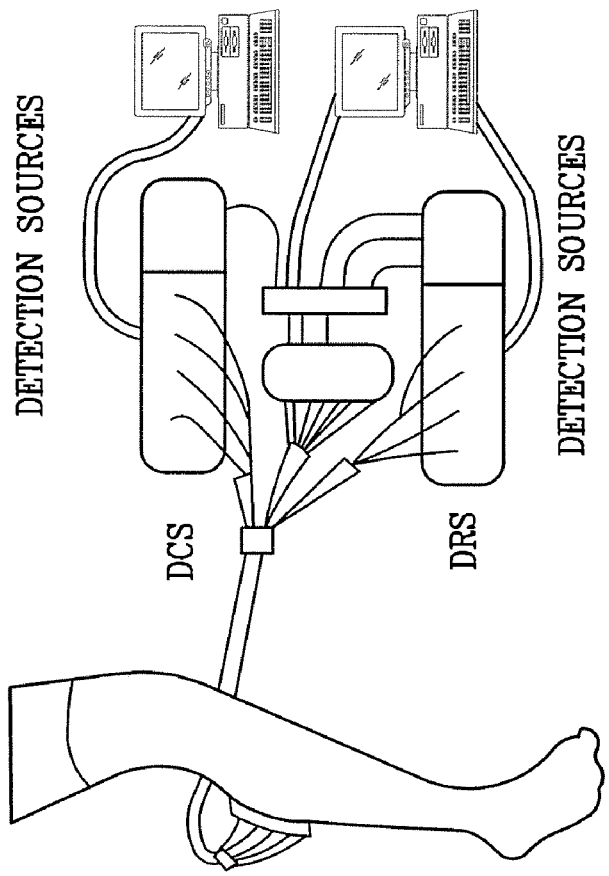
FIG. 2 provides a schematic diagram of the hybrid instrument combining diffuse correlation spectroscopy (DCS) and diffuse reflection spectroscopy (DRS) for measuring of bloodflow and oxygenation, according to the invention.
Figure 2:
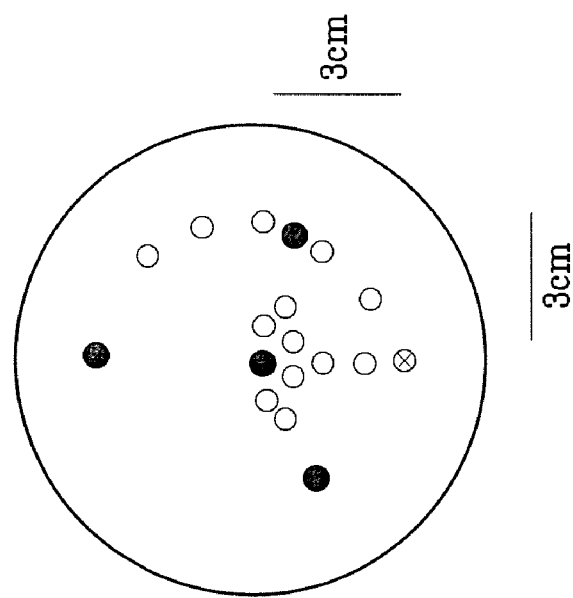

FIG. 2 provides a schematic diagram of a hybrid measurement instrument. The hybrid instrument may employ lasers having two or more wavelengths (e.g., in this case 676 nm, 786 nm, 830 nm) that are modulated at 70 MHz to perform diffuse reflection spectroscopy (DRS). A continuous wave laser with a relatively long coherence length (e.g. at 800 nm) may be used for diffuse correlation spectroscopy (DCS). As illustrated in FIG. 2, the probe may include any number of possible configurations including a DCS source (cross) fiber located at the center of eight DCS detector fibers. Also, the probe may include four DRS detector fibers and six DRS source fibers (empty circle) arranged on a 3 cm radius circle. It should be appreciated that a flexible material (e.g., silicone) may be used to tightly hold the fibers in place, and elastic straps may be used to maintain the probe in proximity to the muscle.

Source-detector separation may range, for example, from 0.5-3 cm for DCS and 0.5-6 cm for DRS. The sampling time for DCS measurement may be approximately 1.5 seconds. A complete frame of data, cycling through all source-detector pairs, was acquired in 2.5 seconds. Also, the probe may employ computer devices to control the DRS and DCS.

Generally, the measurement techniques derive tissue optical properties, for example, hemoglobin concentration and blood oxygen saturation from diffuse reflection spectroscopy (DRS) measurements, and blood flow from diffuse correlation spectroscopy (DCS) measurements.

First, DRS for blood oxygenation, the tissue is modeled as a semi-infinite homogeneous medium. A wavelength-dependent semi-infinite analytical solution to the photon diffusion equation can be used to fit for the optical properties of the underlying tissue. Other models, numerical and analytical based on the diffusion equation are used to analyze more heterogeneous (e.g., largest tissues). The properties of the tissue may be characterized by a number of techniques. For example, the optical properties of the tissue may be characterized by an absorption coefficient $\mu_a$ and a reduced scattering coefficient $\mu_s'$.

The multi-distance and multi-wavelength DRS measurements of diffusive waves on the tissue surface provide information about tissue absorption ($\mu_a$ has been dubbed "diffusing wave"). The wavelength-dependent optical absorption coefficient may then be decomposed into contributions from different tissue chromophores, i.e., $\mu_a(\lambda)=\Sigma_i \epsilon_i(\lambda)c_i$. The sum is over all relevant tissue chromophores; $\epsilon_i(\lambda)$ is the extinction coefficient as a function of wavelength for the $i^{th}$ chromophore, and $c_i$ is the concentration of the $i^{th}$ chromophore. The $c_i$ are unknowns to be reconstructed from the wavelength-dependent absorption information. Oxy- and deoxy-hemoglobin concentrations (e.g., $CHbO_2$, $CHb$ respectively) along with water lipid concentration typically are the largest tissue absorbers in the NIR. Combinations of these parameters yield tissue total hemoglobin concentration ($THC=CHb+CHbO_2$) and tissue blood oxygen saturation ($S_tO_2=[CHbO_2/(CHb+CHbO_2)]\times 100$), as well as tissue scattering.

Next, DCS for relative blood flow, consider speckle fluctuations of the diffuse light that are sensitive to the motions of tissue "scatterers," for example red blood cells. The quantity containing this information is the electric field (E(r,t)), and the electric field temporal autocorrelation function. $G_1(r, t)=<E(r,t) E^*(r, t+\tau))>$, or its Fourier Transform is related to the motion of the red blood cells. Here the angle brackets < > denote averages over time and $\tau$ is called the correlation time.

The study of motions in deep tissues is available because the electric field temporal autocorrelation function for light traveling in highly scattering media obeys typical correlation diffusion equation techniques. The correlation diffusion equation can have different forms depending on the nature of the particle motion, and on the variations of these motions with respect to position in the sample. For example, for the random flow that can arise in the tissue vasculature, the mean-square displacement, ($<\Delta r^2(\tau)>$), of the scattering particles (e.g., blood cells) in time $\tau$ is $(\Delta r^2(\tau)>=V^2)\tau^2$. Here, $(V^2)$ is the second moment of the cell speed distribution. In this case the correlation function $G_1(r,\tau)$ will decay approximately exponentially in $\tau$. Its decay rate, $\Gamma(sec^{-1})$, depends on a parameter $\alpha$ (proportional to the tissue blood volume fraction), and on the motion of blood cells. Relative changes in $\Gamma(sec^{-1})$ correspond to relative changes in blood flow.

For blood oxygenation and flow in different layers the investigated tissue is layered (e.g., skin, adipose tissue and muscle or skull and cortex). Based on diffusion theory, the most probable penetration depth of diffuse light in tissue is roughly one-half to one-third the separation of source detector pairs on the tissue surface. In other words, the blood oxygenation and hemoglobin characteristics are derived based on the positioning of the source detector. Therefore, specific source-detector separation pairs provide information about particular tissue layers. Relative blood flow (rBF) in specific layers may be obtained using the DCS data derived from a corresponding single source-detector pair with appropriate separation. Similarly, DRS data from the same source-detector pair may be normalized with its baseline value to calculate the relative change of tissue blood oxygen saturation ($\Delta S_tO_2$) for the corresponding layer. Also, absolute baseline $S_tO_2$ may be estimated from multi-distance DRS measurement. Multi-distance DRS and DRS measurements may also be used to derive images of these quantities based on diffusion equation analysis.

In the calculating blood oxygenation and flow, nominal influence on calculation accuracy was determined by the assumed baseline value of the scattering coefficient $\mu_s'$. Furthermore, even this nominal error may be avoided by employing additional source fibers and by calibrating the coupling coefficients of the instrument more accurately.

Tissue metabolic rate of oxygen consumption ($TMRO_2$) may be modeled in a similar manner as is done with the cerebral metabolic rate of oxygen consumption ($CMRO_2$). In particular, $TMRO_2$ may be calculated by combining the blood flow data and oxygen saturation data. In steady-state, $TMRO_2$ depends on the difference in oxygen concentration across the vasculature (i.e., arteriole minus venous) multiplied by the blood flow rate, or $TMRO_2=(OEF)\times(BF)\times([O_2]_a)$, an equation sometimes referred to as Fick's Law, where $[O_2]_a$ is the arterial oxygen concentration, OEF is the oxygen extraction fraction defined as $([O_2]_a-[O_2]_v)/([O_2]_a)$, and where subscripts v and a denote venous and arterial sides, and where BF is tissue blood flow. This is a general equation typically used in analysis of oxygen metabolism problems, particularly those associated with activation in brain and muscle. It could be replaced with any other adequate model.

Assuming the arterial oxygen concentration, $[O_2]_a$, does not change, the relative change in oxygen metabolism can be shown to be: $rTMRO_2=rOEF\times rBF$, where r denotes relative change, and where differential changes in the temporal decay of diffuse photon correlation functions yield rBF. Also, the oxygen extraction fraction, OEF, is further related to tissue blood oxygen saturation. Therefore, the DCS measurement allows for a determination of relative blood flow, rBF, and the DRS measurements enables a determination of rOEF, where $OEF=(S_aO_2-S_tO_2)/(\gamma \times S_aO_2)$ where $S_aO_2$, and $S_tO_2$ are arterial and tissue saturations respectively, and $\gamma$ indicates percentage of blood volume contained in the venous component of the vascular system. OEF can be obtained direct from the measured $S_tO_2$. Also, if $\gamma$ remains constant, then the compartment parameter divides out of the measure of rOEF.

The measured responses permit derivation of time curves for tissue oxygen saturation (% $S_tO_2$), total hemoglobin concentration (THC (μM)) and relative blood flow (rBF (%)). For example, a time curve for relative tissue metabolic rate of oxygen consumption ($rTMRO_2$ (%)) may be determined for plantar flexion exercise used in exercise rehabilitation and therapy. $TMRO_2$ does not substantially change ($rTMRO_2=1$) throughout the arterial occlusion because there is no functional activity during ischemia. Therefore, a linear regression of the oxygen desaturation rate occurring during the first 60 seconds of ischemia can be used for calculating the $TMRO_2$ level at rest.

Figure 3:
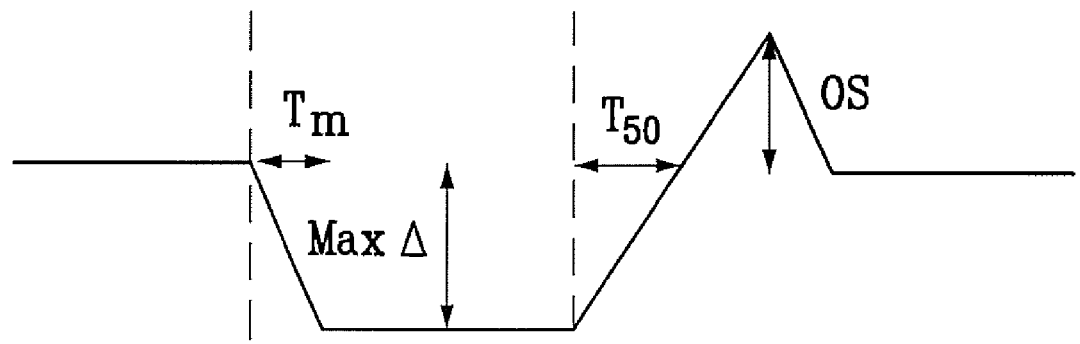
FIG. 3 provides a characterization of the flow response during cuff-occlusion, according to the invention.

To characterize hemodynamic responses, mean and standard deviation are tabulated for maximal change (Max Δ), wave time constants from manipulation onset ($T_m$ (sec)) to maximal response, recovery half-times ($T_{50}$ (sec)) and amount of overshoot (OS (Δ)). FIG. 3 shows an example for characterization of the blood flow response (rBF) during a cuff occlusion. Other variables (e.g., $S_tO_2$, THC and $rTMRO_2$) during cuff occlusion and exercise may be characterized in the same manner.

Figure 4:
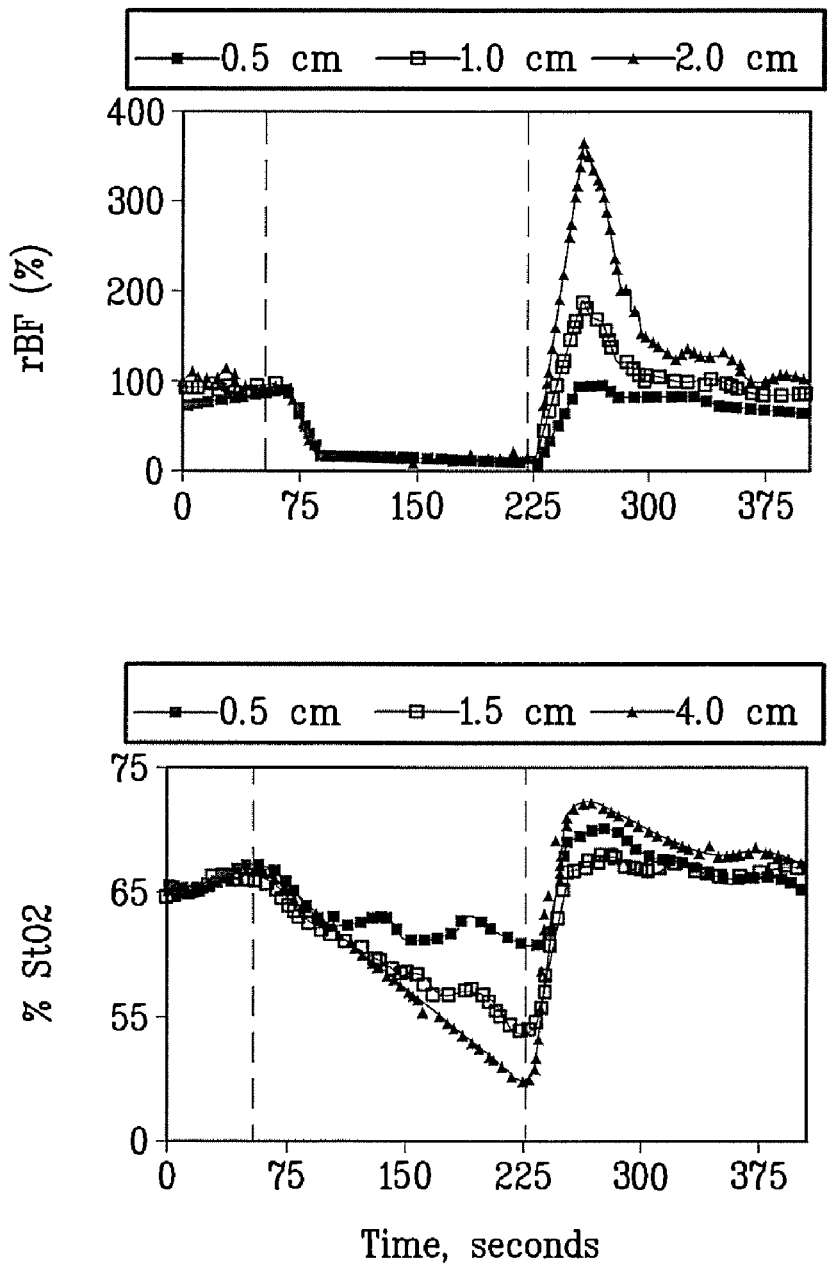
FIG. 4 provides a time curve of relative blood flow and tissue oxygen saturation during arterial occlusion from different source-detector pairs measured on a healthy leg, according to the invention.

FIG. 4 shows the rBF (top) and $S_tC_2$ (bottom) responses during leg arterial occlusion from different source-detector pairs measured on a healthy individual. The source-detector separations, may be any length, for example, 0.5, 1.5, 3, 4, and 5 cm for DRS, and 0.5, 1, 2, and 3 cm for DCS respectively. FIG. 4 indicates that stronger reactive hyperemia (peak flow overshoot) after the release of occlusion, and deoxygenation during occlusion were derived from the separations of 2 cm for DCS and 1.5 cm to 5 cm for DRS, respectively. Similar responses of the different layers were also found in arm cuff occlusion. The stronger responses are mainly from the muscle layer, and separations with the stronger response are used to analyze the data.

Table 1 lists the hemodynamic responses in cuff occlusions from ten healthy volunteers and one PAD patient. % $S_tO_2$ and THC (uM) were fitted using data derived from source-detector separations of 1.5-5 cm and rBF (%) was calculated by averaging signals from the two 2 cm source-detector separations in different locations.

TABLE 1

Responses in cuff occlusions from ten healthy volunteers and one PAD patient.

| Parameters | Subjects | $T_m$ (sec) | Max Δ | $T_{50}$ (sec) | OS (Δ) |
|---|---|---|---|---|---|
| Leg occlusion | | | | | |
| StO2 | Healthy | 177.1 ± 20.7 | −16.4 ± 4.4 | 33.7 ± 26.0 | 3.8 ± 1.7 |
| (%) | PAD | 180.0 | −15.0 | 96.0* | 3.0 |
| THC | Healthy | 88.1 ± 81.9 | −1.8 ± 5.9 | 16.2 ± 18.3 | 2.8 ± 3.1 |
| (μM) | PAD | 25.0 | −10.0 | 36.0 | 5.0 |
| rBF | Healthy | 51.0 ± 11.5 | −90.0 ± 2.4 | 25.6 ± 14.5 | 311.4 ± 90.8 |
| (%) | PAD | 60.0 | −93.0 | 90.0* | 165.0* |
| Arm occlusion | | | | | |
| StO2 | Healthy | 174.7 ± 15.3 | −25.1 ± 8.2 | 19.4 ± 15.2 | 11.4 ± 5.0 |
| (%) | PAD | 180.0 | −23.0 | 23.0 | 10.0 |
| THC | Healthy | 46.6 ± 61.2 | −1.4 ± 6.4 | 13.6 ± 7.3 | 8.6 ± 5.0 |
| (μM) | PAD | 111.0 | −16.0 | 20.0 | 22.0 |
| rBF | Healthy | 14.0 ± 7.4 | −90.3 ± 3.8 | 11.3 ± 6.1 | 445.1 ± 194.1 |
| (%) | PAD | 11.0 | −92.0 | 12.0 | 450.0 |

As noted from Table 1, for healthy volunteers, cuff occlusion of the leg flexor and arm flexor muscles produced a similar response. In particular, the rapid increase of cuff pressure induced a rapid and substantial decrease in rBF: Max ΔrBF=−90.0±2.4% for leg and Max ΔrBF=−90.3±3.8% for arm, assigning a baseline value of 100%. Also, a gradual decrease in $S_tO_2$ occurred throughout the arterial occlusion. The minimum measurable blood flow (−10% of the baseline value) during cuff occlusion is the so-called "biological zero." Also, rBF reached this "biological zero" within the first minute whereas $S_tO_2$ started to decrease rapidly, but did not reach a minimum for approximately 5 minutes.

During cuff occlusion, total hemoglobin concentration (THC) was generally unchanged, however, there was a variation between trials. Also, it was noted that the hemodynamic response trends in the PAD patient are similar to those of the healthy volunteers, and no substantially different responses were found in arm muscle between patient and healthy controls. However, as noted in Table 1, in the patient leg muscle, the relative magnitude of reactive hyperemia was approximately ½ of the controls, and the recovery halftimes of both $S_tO_2$ and rBF after occlusion were about triple the controls.

Figure 5:
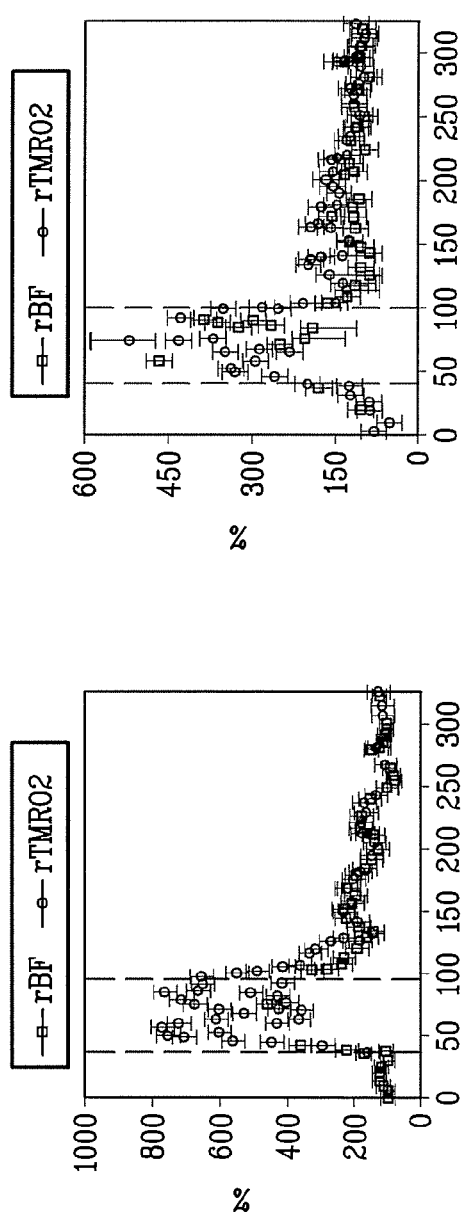
FIG. 5 illustrates hemodynamic responses during one-minute plantar flexion exercise from a healthy individual and a PAD patient, according to the invention.
Figure 5:
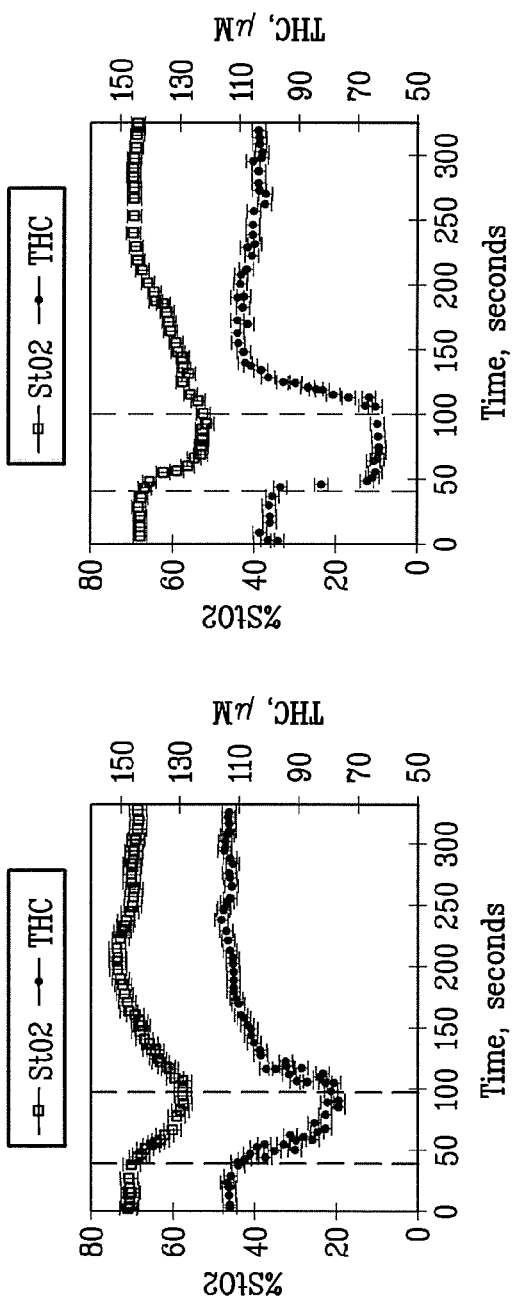

FIG. 5 illustrates the typical time curves of $S_tO_2$ and THC (shown on the top), and rBF and $TMRO_2$ (shown on the bottom) during plantar flexion exercise from a healthy individual (shown on the left) and a PAD patient (shown on the right). rBF during exercise did not show different phases of the muscle activity (contraction and relaxation) due to the comparatively long sampling time (2.5 seconds). In a separate trial with higher temporal resolution (i.e., approximately 1 Hz) achieved by changing the measurement duration for DCS (in expense of lower signal-to-noise ratio) and using only one source position for DRS measurement, flow oscillations that correlated with the muscle contraction and relaxation were exhibited.

Table 2 summarizes the mean± standard deviation from ten healthy volunteers and one PAD patient.

| Parameters | Subjects | $T_m$ (sec) | Max Δ | $T_{50}$ (sec) | OS (Δ) |
|---|---|---|---|---|---|
| StO2 | Healthy | 29.4 ± 8.7 | −17.1 ± 7.9 | 36.7 ± 22.8 | 4.8 ± 3.6 |
| (%) | PAD | 22.0 | −12.3 | 70.0* | 3.0 |
| THC | Healthy | 18.3 ± 9.6 | −17.6 ± 9.9 | 23.7 ± 13.9 | 3.3 ± 3.9 |
| (μM) | PAD | 12.0 | −32.8* | 16.0 | 10.0 |
| rBF | Healthy | 14.9 ± 8.1 | 473.7 ± 138.6 | NA | −9.5 ± 19.5 |
| (%) | PAD | 12.0 | 240.0* | NA | −10.0 |
| rTMRO2 | Healthy | 14.9 ± 8.1 | 694.5 ± 176.5 | NA | −7.5 ± 15.9 |
| (%) | PAD | 12.0 | 338.4* | NA | 0.0 |

The healthy muscle responses showed variations among subjects. Within a short time (14.9±8.1 seconds) after the exercise began, $rTMRO_2$ increased approximately 7 fold (694.5±176.5% assigning a baseline value of 100%). To meet the increase in oxygen demand, rBF increased rapidly and reached a maximum (473.7±176.5%, assigning a baseline value of 100%) in the same short time (14.9±8.1 seconds). This increase in flow during exercise is termed active hyperemia.

The greatest discrepancy between rBF and $rTMRO_2$ occurred in approximately 15 seconds demonstrating the maximum mismatch between oxygen delivery and oxygen demand. THC decreased and reached a minimum (Max ΔTHC=−17.6±9.9 μM) almost as fast as rBF, while $S_tO_2$ started to decrease rapidly and reached a minimum (Max $\Delta S_tO_2$=−17.1±7.9%) in 29.4±8.7 seconds. After reaching the maximum or minimum, those variables fluctuated around their extremes.

Once exercise ceased, rBF and $rTMRO_2$ recovered to their baselines rapidly whereas THC and $S_tC_2$ increased more slowly towards their baselines. The recovery half-time ($T_{50}$) of rBF and $rTMRO_2$ after occlusion were so fast that they were not measurable with the present temporal resolution (i.e., 2.5 second sampling time) of the instrument.

A similar variation was observed between left/right arm/leg of healthy individuals. The PAD patient and the healthy volunteers had similar dynamic response trends to the plantar flexion exercise. The differences between the PAD patient and the healthy volunteers were primarily in magnitude of the active hyperemia (rBF), total hemoglobin concentration (THC) and oxygen consumption rate ($rTMRO_2$) during exercise, and the recovery half-time of $S_tC_2$ after exercise in the leg muscle. The relative magnitudes of active hyperemia, THC and $rTMRO_2$ during exercise were half of the controls, and the recovery half-time of $S_tC_2$ after exercise were double the controls.

Figure 7:
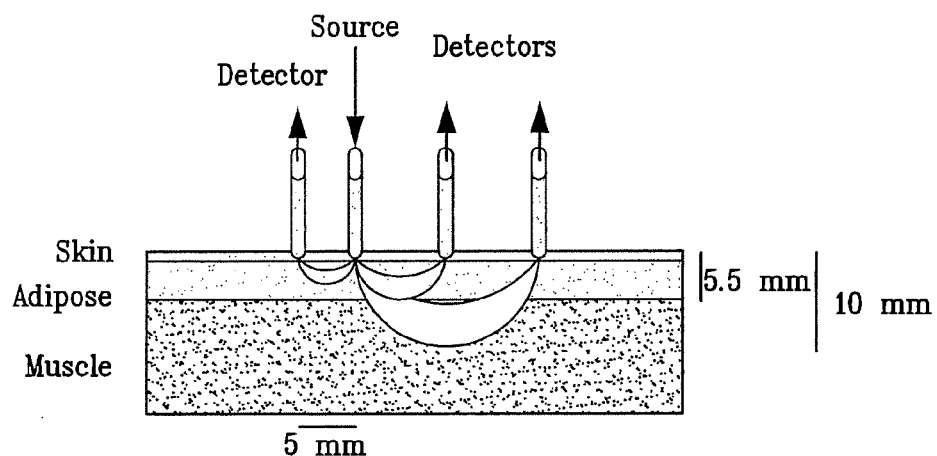
FIG. 7 provides a schematic of a multi-layer tissue model and the simplified presentation of diffuse light penetration in relation to the different source-detector separations, according to the invention.

FIG. 7 displays a multi-layer tissue model and a schematic of diffuse light penetration for the different source-detector separations. In particular, FIG. 7 simulates the configuration of the DCS blood flow measurements in leg. As shown in FIG. 7, the signal detected by the source-detector pair with separation of 2 cm derives mainly from the muscle layer, whereas signals from shorter separations are from upper layers. An accurate quantification of the penetration depth of diffuse light requires consideration of the tissue optical properties and the thickness of each layer, as well as a multi-layer model are necessary. Penetration depth may be estimated by experimentally calibrating using the reactive hyperemia measurement after arterial occlusion release.

Reactive hyperemia, following rapid release of arterial occlusion, is a transient increase in blood flow. The ability of an organ to display reactive hyperemia is related to its ability to display auto-regulation. Different organs display varying degrees of auto-regulatory behavior. For example, skeletal muscle shows moderate auto-regulation, while the cutaneous microcirculation shows little or no auto-regulatory capacity. The reactive hyperemia occurs because during the period of occlusion, tissue hypoxia and a build-up of vasodilator metabolites (presumably dilate arterioles) decrease vascular resistance. When compared with muscle tissue, both oxygen consumption and oxygen extraction are much lower in adipose tissue. Therefore, the lower metabolism accumulates less vasodilator metabolites during arterial occlusion in adipose tissue, inducing lower magnitude of reactive hyperemia.

From FIG. 4 it is noted that the magnitude of reactive hyperemia derived from the source detector separation of 2 cm is more than 2 times greater than those from shorter separations. Taken together, the result derived from the simulation (in FIG. 6) and the measurement (see FIG. 4), suggest that the strongest hyperemia signal (2 cm separation) is derived from the muscle tissue layer, while the weaker responses are due to the source-detector pairs with shorter separations and represent the response of cutaneous tissues.

Similarly, decreases of $S_tC_2$ during arterial occlusion derived from the separation of 1.5 cm to 5 cm are much higher than those from 0.5 cm separation (in FIG. 4), and thus represent response of the muscle layer. These findings suggest that both DRS and DCS can probe through the upper tissue layers into the muscle, based on the choice of source-detector separations in the appropriate range for these measurements.

The hemodynamic responses of healthy muscle tissues have demonstrated comparable and repeatable variations during hemodynamic perturbations. At the onset of the arterial occlusion, blood flow rapidly goes to "biological zero." $S_tO_2$ on the other hand, decreases gradually during the occlusion because of continuous oxygen consumption in tissues and minimal blood flow (oxygen delivery). The declining rate of muscle oxygenation reflects the level of tissue oxygen consumption rate at rest. When the occlusion is released, there is a reactive hyperemia because of the auto-regulation (vasodilation) of muscle vasculature in response to metabolites created during ischemia.

During the hyperemia, oxygen is replenished and the metabolic stimulus for vasodilation is washed out, causing vasoconstriction. Thus blood flow and oxygen return to their normal resting levels respectively. The reactive hyperemia has important physiological implications because it is related to the ability of muscle vasculature to auto-regulate.

Characterization of dynamic exercise is more difficult because of its complexity and the speed of metabolic mechanisms. Exercise consumes large amounts of energy and therefore requires delivery of considerable amounts of oxygen and substrate (e.g., glucose, protein, ion), as well as the removal of waste metabolites (e.g., $CO_2$, $H^+$, lactate). The intrinsic auto-regulation ability in muscle vasculature increases blood flow to meet the increased need for delivery and removal. This increase in flow is termed "active hyperemia" and is often brought about by the reduction of vascular resistance (vasodilation).

Tissue hypoxia and accumulated vasodilator metabolites during exercise dilate arterioles and thus decrease vascular resistance. Moreover, the "skeletal muscle pump" and "vascular recruitment" also facilitate blood flow during muscle exercise. Mean blood flow increases during plantar flexion exercise (in FIG. 5). However, if blood flow is measured without averaging, the flow will be seen in two phases—i.e.,—decrease flow during contraction and increase flow during relaxation.

Figure 6:
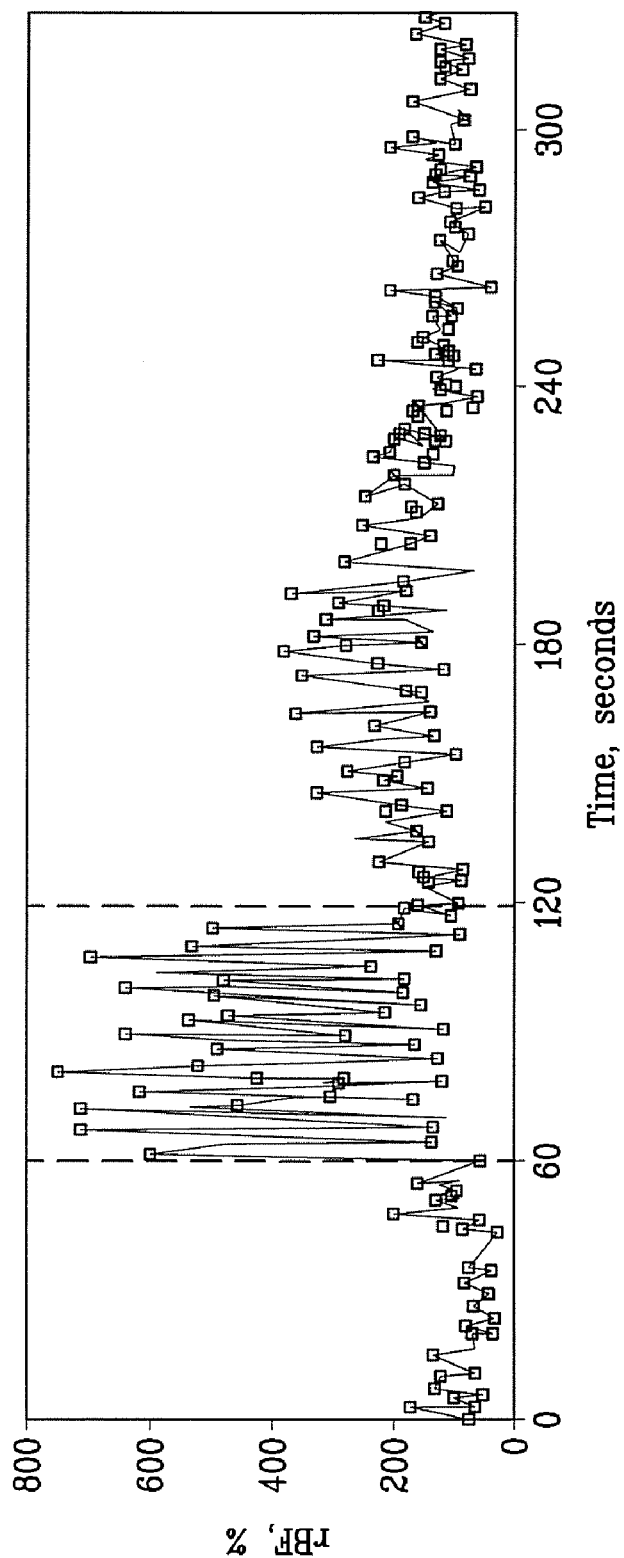
FIG. 6 provides a time curve of relative blood flow during one-minute plantar flexion exercise from a healthy individual, according to the invention.

Using a higher temporal resolution (e.g., approximately 1 Hz), diffuse correlation spectroscopy (DCS) can capture these two phases (in FIG. 6). The increased blood volume during muscle relaxation mainly increases blood in the capillary component as previously "unused" capillaries open (i.e., vascular recruitment). In contrast, the muscle contraction mainly compresses the vascular tree in the venous component propelling blood towards the heart (skeletal muscle pump).

The magnitude of the active hyperemia (i.e., rBF) is closely related to the increase in tissue metabolic rate ($rTMRO_2$) throughout the period of exercise. However, the average increases were quite different (FIG. 5 and Table 3). Also, the average increase in blood flow at the transition from rest to the exercise was approximately 4.7 fold whereas the average increase in $rTMRO_2$ was approximately 7 fold. The increase in rBF was significantly lower than the increase in $rTMRO_2$ ($p=0.006$, two-sample t-test). Therefore, a gradual decrease in tissue oxygenation saturation ($S_tC_2$) was produced, indicating that increased oxygen demand may not be completely met by an increase in blood flow.

The ability to evaluate how muscle blood flow responds to energy demands is a useful assessment tool. For example, the mismatch between blood supply and oxygen demand is considered to be an important factor in determining the cellular depletion of energetic metabolites, and the magnitude of active hyperemia during exercise is believed to be related to the vascular response to these metabolites.

The different responses between healthy volunteers and the PAD patient are illustrated in Table 1 and Table 2. As shown in Tables 1 and 2, the relatively longer recovery half-times of $S_tC_2$ ($T_{50}=96$ seconds for cuff occlusion and $T_{50}=70$ seconds for exercise) were found in a diseased leg. Also, a longer recovery half-time of rBF ($T_{50}=90$ seconds) was also found in the diseased leg after release of the cuff occlusion. In addition, as shown in Table 2, the magnitude of active hyperemia (rBF) and $rTMRO_2$ during the exercise in the diseased leg were only half of those in healthy volunteers.

As shown in Table 1, a similar observation was found in the magnitude of reactive hyperemia during the arterial occlusion in the diseased leg. These weaker flow (dilation) responses may help determine the affecting the oxygen delivery and ability to support muscle metabolism. As shown in Table 2, less blood flow delivery during exercise in the diseased leg leads to a greater decrease of tissue total hemoglobin concentration (THC).

In sum, the novel techniques permit DCS to penetrate through layers of upper tissues to muscle tissue. As a result, this technique provides more accurate measurement of blood flow in muscle capillary bed compared than currently available. This is because the technique is not adversely affected by the blood flow from the surrounding tissues (e.g., cutaneous tissues, bone, tendons). The DCS technique does not interrupt the blood flow during measurement. Also, because of the ease of its noninvasive nature, the technique can be used in different dynamic conditions. The efficacy of the novel technique for DCS flow variation is approximately 7.6 times lower than MRI flow variation techniques.

Also, the combination of DCS and DRS techniques has permitted the use of both optical techniques non-invasively and continuously to measure rBF, $S_tO_2$ and THC in deep muscle tissues under rest as well as during mild exercise and extreme cuff occlusion perturbations. These hemodynamic parameters permit an estimation of the changes of index $rTMRO_2$. Also, these techniques permit portable and relatively inexpensive hybrid instrumentation that may be conducted in a clinical routine examination. Quantification of hemodynamic responses (e.g., reactive hyperemia, active hyperemia, mismatch between blood supply and oxygen demand, recovery half-time) is also useful for estimation of physiological states. Such information may facilitate improved diagnostic and treatment options for patients with PAD.

Figure 8:
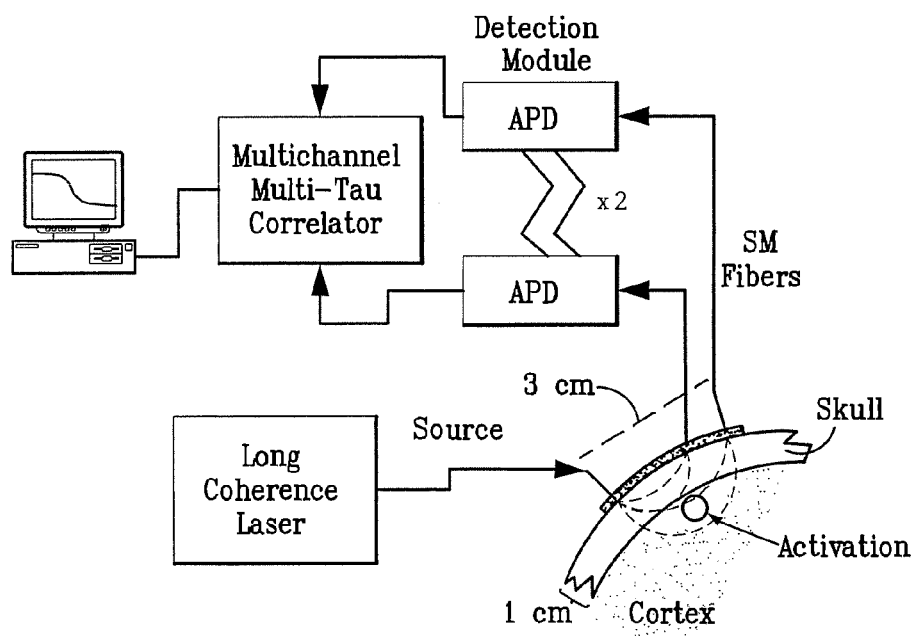
FIG. 8 provides a block diagram of a basic DCS detection module, according to the invention.
Figure 9:
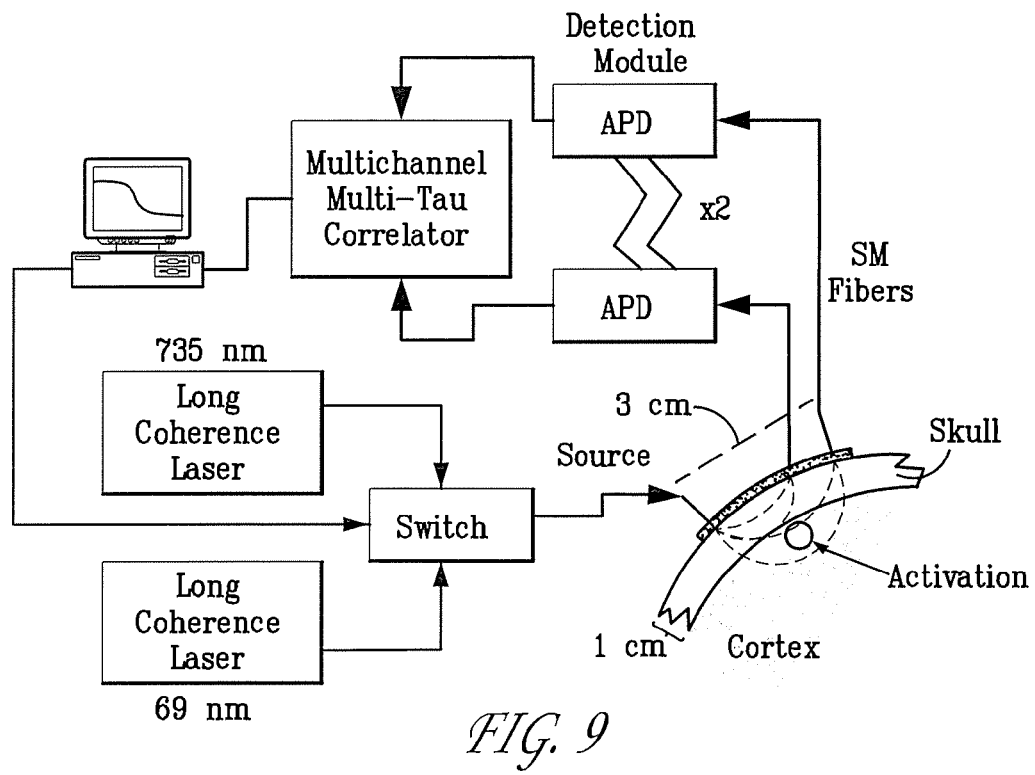
FIG. 9 provides a block diagram of another DCS detection module, according to the invention.

The novel techniques also facilitate treatment and detection of various other maladies. FIGS. 8 and 9 provide an illustration of a probe that uses DCS and DRS techniques. FIG. 8 illustrates a block diagram of a basic DCS detection module and FIG. 9 provides a diagram of a DCS detection module using two laser devices.

FIG. 8 provides a block diagram of a basic DCS detection module. The novel apparatus employs high quality single-mode fibers that operate in certain wavelengths (e.g., 800 nm) and that are isolated from light leaks. The detector is a fast, photon counting avalanche photodiode (APD) with low dark current, for example a model SPCM-AQR-14, manufactured by Perkin-Elmer of Canada. The APD may include an amplifier-discriminator unit that outputs a standard TTL signal corresponding to the number of photons counted. This signal may be fed to a fast, multi-Tau correlator board. These boards are software configured and are available in multi-channels.

One curve is obtained by the device every 106 ms. Each individual curve may be outputted or an average of many curves may be outputted. The signal-to-noise ratio increases with the square root of the number of curves averaged. The multi-Tau technique uses a quasi-logarithmic spacing of the temporal bins allowing collection of a large range of delay times with a limited (e.g., 255) channels which is essentially equivalent to using 255 independent correlators with increasing delay times (doubled at each octave).

Correct choice of the bin spacing avoids triangular averaging related errors and is defined by the correlator hardware. The output from the correlators may be combined to obtain the desired autocorrelation function. This method improves the signal-to-noise while keeping a large dynamic range (in delay times) and therefore, the efficiency.

A DCS light source module may be a long coherence laser, for example, a diode pumped laser diode working at continuous wave mode, for example, a 800 nm, model TC40, manufactured by SDL Inc, of San Jose, Calif.). The light at several separations (e.g., 1.5, 2.0, and 3.0 cm) are detected and the temporal autocorrelation functions are calculated by the correlator board. The multi-channel design enables adequate signal-to-noise by averaging some curves (i.e., 1060 ms per data-point).

In addition, a second laser source may be added as shown in FIG. 9. The second laser source may be a 690 nm laser manufactured by Crystal Laser and a 2×1 optical switch to share source positions, as shown in FIG. 4. Also, the laser source may be connected via an electrical switch so as to share detectors. Using a second laser doubles the data acquisition time (e.g., approximately 2 seconds), and also enables simultaneous measurements of tissue oxygenation. The computer controlled optical switch may be used to share the source fiber between two lasers. This is accomplished by recording the detected, average intensity at each detector position and each wavelength and using continuous wave near-infrared spectroscopical methods, well known to those skilled in the art.

Although not shown it should be appreciated that the device may include various other components well known to those skilled in the art, including but not limited to, CCD camera, photomultiplier, photodiode, avalanche diode, photomultiplier tubes, etc.

A DCS analyzer may be used to analyze blood flow. In particular, as is well known to those skilled in the art, blood flow data is analyzed by fitting each autocorrelation curve to a model, for example, a semi-infinite, many layer diffusion model. The flow measurements yield relative CBF (rCBF). For quantification, the partial volume effects may be reduced by using a two layer model with the top layer (skull) thickness set at 1 cm with a flow less than 1% of the bottom layer (brain). Similarly, the CW intensity data at both wavelengths will be fit to a multi-distance, two-layer diffusion model, yielding the oxy- and deoxyhemoglobin concentrations. Tissue oxygen saturation and total hemoglobin concentration may be calculated from these measurements.

The novel extraction of two different data types enables relative changes in $CMRO_2$ ($rCMRO_2$) to be derived from the measured variation in blood flow, deoxy-hemoglobin concentration, and total hemoglobin concentration. In this model, a constant arteriol-venous tissue compartmentalization may be assumed, and for slow variations (i.e., approximately a few seconds), $rCMRO_2$ is found to be proportional to the product of rCBF and relative changes in deoxy-hemoglobin and total hemoglobin concentration.

Figure 10:
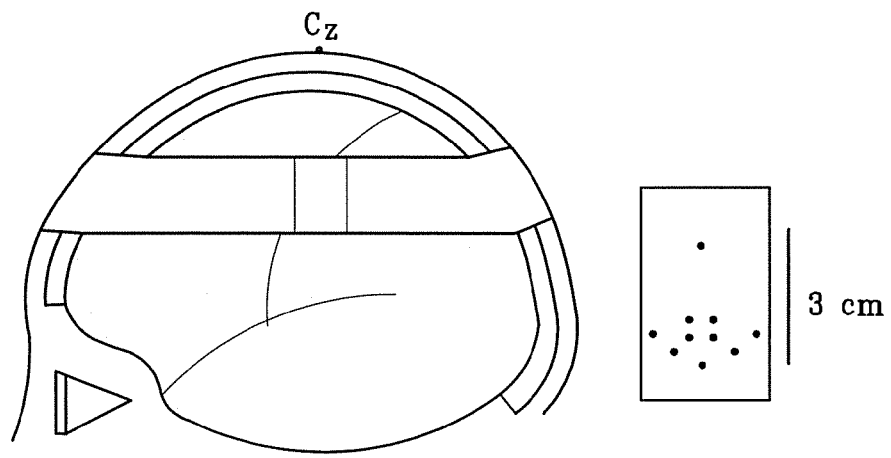
FIG. 10 illustrates placement of a device on a patient's head, according to the invention.

One set of applications involves the study, diagnosis, monitoring and treatment of the brain. In particular, DCS probe may be used to study functional activation of the human brain. FIG. 10 illustrates placement of the device on the patient's head to facilitate such investigation of the brain. Eight DCS detectors may be used, for example, at 2 cm (×2), 2.5 cm (×2) and 3 cm (×4) distance from a source placed at the center of a circle (radius=3 cm). The probe may be fastened using elastic, medical bandages. The fibers may be custom built with special ferrules at the end and are held in place.

Figure 11:
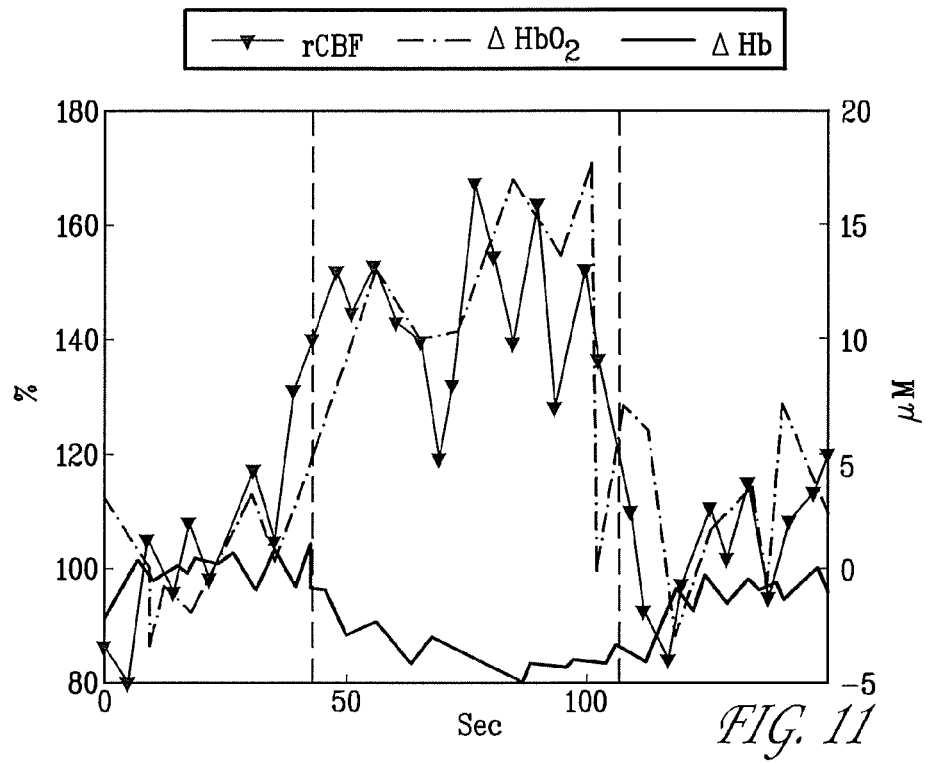
FIG. 11 shows a corrected hemoglobin concentration and flow changes, according to the invention.
Figure 12:
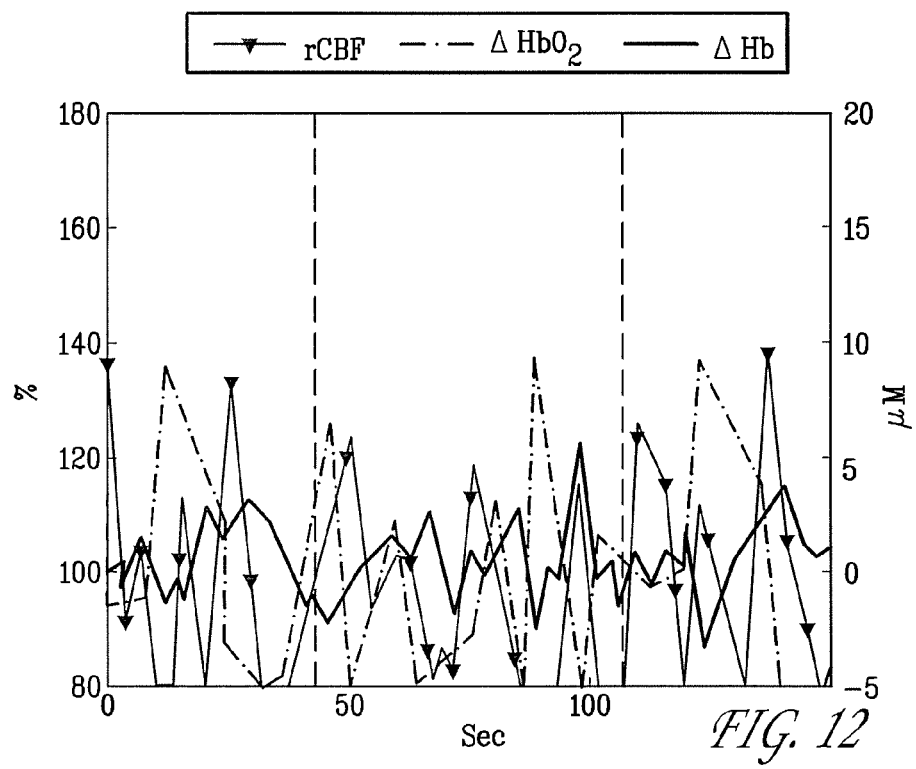
FIG. 12 shows another corrected hemoglobin concentration and flow changes, according to the invention.
Figure 13:
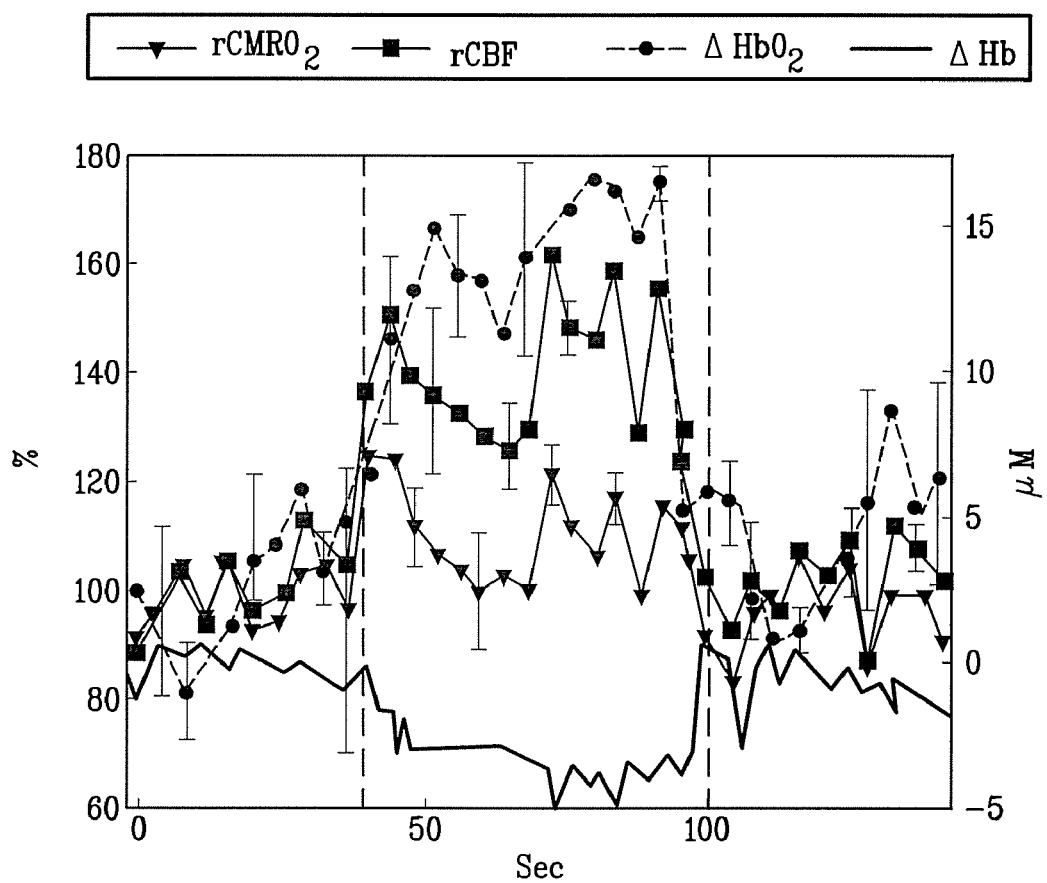
FIG. 13 shows another corrected hemoglobin concentration and flow changes, according to the invention.

In one study, illustrated with respect to FIGS. 11-13, a patient was instructed to tap their index and middle fingers against the thumb at 3 Hz, in time with an auditory cuing signal. A 1-min baseline was recorded before and after each stimulus, and a blocked design of 15 such stimuli was used. One patient was asked to repeat the study using the ipsilateral hand to confirm the contralateral nature of the optical response, and with another subject 30 seconds of stimulus were obtained, and signals were compared with those of 1 minute stimulus duration.

FIG. 11 shows the corrected hemoglobin concentration and flow changes. The graph in FIG. 11 indicates a sustained rise in oxyhemoglobin, a decrease in deoxyhemoglobin, with an increase in CBF. FIG. 12 illustrates that if the probe was placed 2 cm frontal to the motor cortex, the effect of the finger tapping was clearly absent, demonstrating the local nature of the response. FIG. 13 illustrates that the increase in $CMRO_2$ due to finger tapping was 10.1±4.4% within the range of values (9%-29%) from hybrid MRI measurements. The ratio of rCBF to $rCMRO_2$ is 3.8±1.1.

Notably, when the stimulus duration was 30 seconds instead of 60 seconds, the measured amplitude did not change significantly, but the peak duration was halved. No response was visible on the side ipsilateral to the stimulated hand, and measurements when the probe was placed far away from the sensorimotor cortex did not exhibit any significant changes in signal. Therefore, this investigation validates that the efficacy of the hybrid instrument that combines diffuse optical and correlation spectroscopies to measure concurrent variations of blood flow, blood oxygenation, and oxygen metabolism through the intact skull of an adult human brain during sensorimotor cortical activation. Metabolism may be determined using a bulk overall value technique, and may be measured at one or more locations. Blood metabolism may be measured as two dimensional or three dimensional images.

In another application, many sick infants are admitted to the pediatric neuro-intensive care unit (PNICU) with severe cerebral hypoperfusion due to cardiac disease as well as other conditions. The management of these individuals is complicated due to their age and fragility. Yet, infants are more able to benefit from the novel techniques because an infant's skull is thinner and even more transparent than an adult patient. Also, these novel techniques can provide the ability to do extensive research on the nature and progress of disease in comparison to the development of healthy infants. Another application for the novel techniques involves sleep studies of patients with sleep disorders. Patients with symptoms indicating sleep disorders such as sleep apnea are regularly diagnosed through a series of doctor visits with different specialties and tests of varying complexity. The diagnosis of sleep apnea is complicated because many factors can disturb sleep. The novel technique can improve the acquisition of data related to sleep disorders because cerebral blood flow can be monitored regionally and continuously and can be related to the brain metabolic state, without significantly disturbing the patient's normal sleep process.

The novel techniques described also may be used for the monitoring of stroke patients. A critical improvement to the treatment and management of patients who had suffered a stroke is the ability, provided by the novel techniques, to monitor the brain metabolism locally and continuously.

Another application involves cerebral monitoring of cardiac surgery patients. Often, cardiac surgery patients undergoing by-pass surgery have cerebral injury due to surgery. Using traditional techniques for cerebral monitoring, like invasive methods such as Licox probes are limited because patients having bypass surgery are placed on heparin (a blood thinner) at surgery. This blood thinner induces a high risk of a brain hemorrhage. The novel techniques allow for the cerebral monitoring during bypass surgery without using invasive techniques whose side effects may aggravated by the necessary blood thinners.

Another application of the inventive techniques involves the prediction of treatment efficacy in radiation-induced fibrosarcoma (RIF) tumors. A non-contact probe having source/detector fibers on the back image-plane of a camera may be used to avoid potentially compressing the tumor and altering blood flow. The lens of the camera may be approximately 15 cm away from the tumor, allowing unobstructed illumination with the treatment light at a small angle to the perpendicular. Also, the novel techniques have use in assessing therapeutic interventions to different cancers in various organs, including the head, neck, prostate, breast and brain, for example, and in determining efficacy of drugs used to teat cancers during photodynamic therapy, well known to those skilled in the art. Also, the technique may be used to monitor or assess severity or treatment benefits of tissue damage due to stroke, trauma, cardiovascular disease and other maladies.

The optical fibers for the sources and detectors may be bounded and arranged in a two-dimensional pattern to cover the whole tumor area. The largest source detector separation was 2.5 mm. An optical filter mounted in front of the camera lens attenuated light below 650 nm, enabling blood flow to be monitored, for example, using a 630 nm illumination. The sampling time for one scanning frame (13 sources and 4 detectors) may be set at approximately 18 seconds.

DCS may be used to continuously monitor blood flow during PDT (from 15 minutes before PDT to 15 minutes after PDT). Additional measurements may be performed, for example, at times 3, 6.5 and 24 hours after PDT. Treatment efficacy may be estimated by measuring the number of days required for tumor regrowth to a volume of 400 mm$^3$ (Time-to-Regrowth). A linear-to-log regression may be used to estimate and test for statistically significant correlations between the blood flow responses and the treatment efficacy.

Rapid vascular occlusion during PDT compromises the tissue oxygen supply, which in turn reduces PDT efficacy. Conversely, larger reductions in relative blood flow at 3 hours after PDT demonstrate permanent vascular damage, which correlates with good treatment efficacy. Therefore, the blood flow responses to PDT can be used to predict/evaluate treatment efficacy.

The novel techniques also may have some efficacy in providing clinical measurements in the human prostrate. In particular, the novel techniques allow for a real-time diffuse optical PDT dose monitoring system for ultrasound-guided interstitial human prostate PDT by determining in-vivo tissue optical properties, photosensitizer concentration, tissue blood oxygenation, and blood flow, before, during and after PDT in human prostatic carcinoma.

What is claimed:

1. A method for determining one or more characteristics of tissue of a subject, the subject having a surface exposed to at least one light source, the method comprising:
    measuring a motion of moving scattering particles in the tissue,
        wherein the motion of the moving scattering particles is derived at least in part from light field fluctuations,
        the light field fluctuations measured, at least in part, by a light temporal autocorrelation function,
        the light field fluctuations caused, at least in part, by the moving scattering particles in the tissue and transmission of light through the tissue, the light produced by the least one light source;
    measuring blood oxygenation, oxy and deoxy-hemoglobin characteristics, hemodynamic characteristics, and scattering characteristics of the tissue,
        wherein the blood oxygenation, oxy and deoxy-hemoglobin characteristics, hemodynamic characteristics, and scattering characteristics are derived, at least in part, from the transmission of light through the tissue with respect to a wavelength of light,
        the oxy and deoxy-hemoglobin characteristics being further derived from absorption effects and scattering effects of the tissue on the transmitted light;
    determining blood flow rate characteristics based at least in part on collected optical data, the collected optical data based, at least in part, on the motion of the moving scattering particles, the absorption effects of the tissue, and the scattering effects of the tissue; and
    determining oxygen metabolism of the tissue and changes of the tissue based at least in part on the blood flow rate characteristics and the oxy and deoxy-hemoglobin characteristics,
        at least a portion of the tissue being at least one centimeter beneath the surface.

2. The method of claim 1, wherein the blood oxygenation and hemoglobin characteristics are further derived as a function of a position of a source detector.

3. The method of claim 2, wherein, the source detector and light source are separated by at least about 2 centimeters.

4. The method of claim 1, wherein the tissue is a portion of at least one of the following: brain, muscle, breast.

5. The method of claim 1, wherein the tissue is a portion of a tumor bearing organ including at least one of the following: head, neck, prostate, breast, or brain.

6. The method of claim 1, wherein the tissue is at least one of the following: layered or heterogeneous.

7. The method of claim 1, wherein the tissue characteristics are measured during exercise.

8. The method of claim 1, wherein the tissue characteristics are measured during functional activation.

9. The method of claim 1, wherein the tissue characteristics are measured during a presence of tissue damage due to stroke.

10. The method of claim 1, wherein the tissue characteristics are measured during a presence of tissue damage due to trauma.

11. The method of claim 1, wherein the tissue characteristics are measured during a presence of tissue damage due to cardiovascular disease.

12. The method of claim 1, further comprising determining a velocity of a blood cell in the tissue.

13. The method of claim 1, further comprising determining a motion of cell organelles in the tissue.

14. The method of claim 1, further comprising determining fluctuations of cell organelles in the tissue.

15. The method of claim 1, wherein the blood flow rate and the oxygenation are measured simultaneously.

16. The method of claim 1, further comprising monitoring peripheral vascular disease.

17. The method of claim 1, further comprising monitoring therapeutic interventions to cancers in organs.

18. The method of claim 1, further comprising monitoring effects of cardiovascular disease on muscles.

19. The method of claim 1, further comprising monitoring effects of cerebrovascular disease on brain well-being and function.

20. The method of claim 1, further comprising determining an efficacy of exercise rehabilitation.

21. The method of claim 1, further comprising determining an efficacy of cancer therapy.

22. The method of claim 1, further comprising determining an efficacy of tumor treatment and therapy.

23. The method of claim 1, further comprising monitoring peripheral vascular disease.

24. The method of claim 1, further comprising determining efficacy of a drug used to facilitate blood flow.

25. The method of claim 1, further comprising determining efficacy of a drug used to treat cancers during photodynamic therapy.

26. The method of claim 1, wherein the tissue is human.

27. The method of claim 1, wherein the tissue is animal.

28. The method of claim 1, wherein the measurements are taken without a probe penetrating the subject's scalp and skull.

29. The method of claim 1, wherein the measurements are taken non-invasively.

30. A device for analyzing tissue, comprising:
    a first light source configured to apply a light to the tissue;
    at least one light detector, the at least one light detector configured to detect at least a quantity of light transmitted through the tissue and light field fluctuations caused, at least in part, by moving scattering particles in the tissue; and a computer processor in communication with the at least one light detector, the computer processor being configured to:

determine a motion of the moving scattering particles in the tissue, the motion of the moving scattering particles being derived at least in part from the light field fluctuations, the light field fluctuations measured, at least in part, by a light temporal autocorrelation function;

determine blood oxygenation, oxy and deoxy-hemoglobin characteristics, hemodynamic characteristics, and scattering characteristics of the tissue, the blood oxygenation, oxy and deoxy-hemoglobin characteristics, hemodynamic characteristics, and scattering characteristics being derived, at least in part, from transmission of light through the tissue with respect to a wavelength of the light, the oxy and deoxy-hemoglobin characteristics being further derived from absorption effects and scattering effects of the tissue on the transmitted light;

determine blood flow rate characteristics based at least in part on collected optical data, the collected optical data based, at least in part, on the motion of the moving scattering particles, the absorption effects of the tissue, and the scattering effects of the tissue; and determine oxygen metabolism of the tissue and changes of the tissue based at least in part on the blood flow rate characteristics and the oxy and deoxy-hemoglobin characteristics, at least a portion of the tissue being at least about one centimeter beneath the surface.

31. The device of claim 30, further comprising an optical switch that shares light source positions.

32. The device of claim 30, further comprising an electrical switch that shares more than one light detector.

33. The device of claim 30, further comprising at least one of the following: photodiodes, avalanche photodiodes, photomultiplier tubes, and CCD camera.

34. The device of claim 30, wherein a fast CCD camera or photomultiplier is used as a detector.

35. The device of claim 30, further comprising a computer having a computer-readable medium with computer-executable instructions, wherein the computer-executable instructions calculate a correlation function.

36. The device of claim 30, further comprising a component to measure flow of externally injected microspheres through vasculature.

37. The device of claim 30, further comprising at least one other light detector.

38. The device of claim 30, wherein blood metabolism is measured using a bulk overall value technique.

39. The device of claim 30, wherein the oxygen metabolism is determined at one or more locations.

40. The device of claim 30, wherein the oxygen metabolism is determined as two dimensional images.

41. The device of claim 30, wherein the oxygen metabolism is determined as three dimensional images.

42. The device of claim 30, wherein the light source and light detector are separated by at least about 2 cm.

* * * * *

UNITED STATES PATENT AND TRADEMARK OFFICE
CERTIFICATE OF CORRECTION

| | | |
|---|---|---|
| PATENT NO. | : 8,082,015 B2 | Page 1 of 1 |
| APPLICATION NO. | : 11/106390 | |
| DATED | : December 20, 2011 | |
| INVENTOR(S) | : Arjun G. Yodh et al. | |

It is certified that error appears in the above-identified patent and that said Letters Patent is hereby corrected as shown below:

In the Specification

Column 1, Line 12, insert:
-- GOVERNMENT INTEREST
This invention was made with government support under HL057835, MH059934, and NS033785 awarded by the National Institutes of Health. The government has certain rights in the invention. --

Signed and Sealed this
Sixteenth Day of May, 2023

Katherine Kelly Vidal
*Director of the United States Patent and Trademark Office*